US006759253B2

United States Patent
Usui et al.

(10) Patent No.: US 6,759,253 B2
(45) Date of Patent: Jul. 6, 2004

(54) PROCESS MONITORING METHODS IN A PLASMA PROCESSING APPARATUS, MONITORING UNITS, AND A SAMPLE PROCESSING METHOD USING THE MONITORING UNITS

(75) Inventors: Tatehito Usui, Niihari (JP); Tetsuo Ono, Iruma (JP); Ryoji Nishio, Mito (JP); Kazue Takahashi, Kudamatsu (JP); Nobuyuki Mise, Niihari (JP)

(73) Assignee: Hitachi, Ltd., Tokyo (JP)

( * ) Notice: Subject to any disclaimer, the term of this patent is extended or adjusted under 35 U.S.C. 154(b) by 498 days.

(21) Appl. No.: 09/788,629

(22) Filed: Feb. 16, 2001

(65) Prior Publication Data

US 2001/0014520 A1 Aug. 16, 2001

(30) Foreign Application Priority Data

Feb. 16, 2000 (JP) ........................................ 2000-043575
Jul. 19, 2000 (JP) ........................................ 2000-219557

(51) Int. Cl.[7] ............................................. H01L 21/302
(52) U.S. Cl. ...................... 438/6; 438/7; 438/9; 216/59; 216/60; 156/345.24; 156/345.25; 118/722; 118/728
(58) Field of Search ........................ 156/345.24, 345.25; 216/59, 60; 438/6, 7, 9; 118/722, 728

(56) References Cited

U.S. PATENT DOCUMENTS 5,627,640 A * 5/1997 Chang et al. ................ 356/316

FOREIGN PATENT DOCUMENTS

JP 58-144476 * 8/1993

OTHER PUBLICATIONS

"Use of a Light Emitting Diode as a Current Sensor for Electrostatic Double Probes"; Rev. of Sci. Instru.; vol. 58, No. 2, pp. 315–317; Tendys et. al, Feb. 1987.*
"A Plasmascope Using Light Emitting Diodes"; Rev. of Sci, Instru.; (1–74); vol. 45, No. 1, pp. 57–59; Ejima et, al.*

* cited by examiner

Primary Examiner—George A. Goudreau
(74) Attorney, Agent, or Firm—Antonelli, Terry, Stout & Kraus, LLP

(57) ABSTRACT

The intensity of the light emitted from the light-emitting diode on wafer is measured and then the potential difference between the terminals of the light-emitting element, and the plasma current flowing thereinto are derived from measured light intensity. Since the use of a camera enables non-contact measurement of emitted light intensity, the lead-in terminals for lead wires that are always required in conventional probing methods become unnecessary. In addition, since the target wafer does not require lead wire connection, wafers can be changed in the same way as performed for etching.

33 Claims, 17 Drawing Sheets

TOP VIEW

ENLARGED VIEW OF A-A'
CROSS SECTION ll# PROCESS MONITORING METHODS IN A PLASMA PROCESSING APPARATUS, MONITORING UNITS, AND A SAMPLE PROCESSING METHOD USING THE MONITORING UNITS

BACKGROUND OF THE INVENTION

The present invention relates to methods of measuring potential differences and currents, and, more particularly, the invention relates to methods of measuring the potential difference or the plasma current developed on the surface of a semiconductor wafer sample, when it is under plasma processing, during semiconductor manufacturing processes, with the semiconductor wafer located inside a plasma reactor in order to surface-treat the wafer. Also, the present invention relates to an apparatus for monitoring processes in a plasma processing apparatus by use of the measured potential difference or plasma current, and to a sample processing method that uses the process monitoring apparatus.

In general, during the manufacture of semiconductors, semiconductor wafers need to be subjected to various surface treatment processes, such as etching, and a plasma reactor that applies electromagnetic waves to generate a plasma is most commonly used as the surface processing apparatus. For such a plasma reactor, the electromagnetic waves and the plasma generate a strong electric field not only in the space of the plasma reactor, but also on the surface of the semiconductor wafer mounted on a processing table (sample mount) within the processing apparatus. When a strong electric field is generated on the surface of the semiconductor wafer, the field strength will cause a potential difference on the surface of the semiconductor wafer, and if the potential difference exceeds a predetermined value, the semiconductor wafer may be damaged. It is therefore important to measure the potential difference on the semiconductor wafer surface when processing that surface using a plasma reactor.

In this case, probing (hereinafter referred to as the first known method) is available as one of the typical methods of measuring the electric field strength and potential differences occurring inside the plasma reactor. The first known method is intended to measure the electric field strength and potential differences inside the plasma reactor by inserting conductor probes into a plasma atmosphere and, then, after scanning with the probes, detecting the voltage-current characteristics thereof.

A method of measuring the potential of a semiconductor wafer inside a plasma reactor (hereinafter referred to as the second known method) is described on page 775 of a Japanese-Version Preliminary Article Collection at the 46th Association Symposium on Applied Physics, held in the spring of 1996. For the second known method, the potential difference on the semiconductor wafer surface is measured by searching with probes embedded directly in the semiconductor wafer (which is mounted on the sample mount, namely, the semiconductor wafer mounting table, inside the plasma reactor) at a portion where the potential difference is estimated to occur, instead of searching with probes embedded in the sample mount itself.

Since the first known method, which proposes to measure the potential difference on the semiconductor wafer inside the plasma reactor, is used to detect the voltage-current characteristics of the conductor probes by scanning in a plasma atmosphere, it is necessary to transmit detection output signals from the conductor probes to an external apparatus by using connection lead wires and to provide the vacuum chambers with connection lead wire relay terminals, because the plasma is generated inside the vacuum chamber. In addition, the total structure of the plasma reactor is complex, and this makes it impossible for the potential difference on the semiconductor wafer to be measured using a simplified means.

Furthermore, since the second known method, which proposes to measure the potential difference on the semiconductor wafer inside the plasma reactor, uses probes embedded in a sample mount on which the semiconductor wafer is to be mounted, it is not only necessary for the sample mount to be of special structure, but it is also difficult to process the surface of the semiconductor wafer on this sample mount after measuring the potential difference on the semiconductor wafer by use of the sample plate. In addition, the type of sample mount to be used will differ between measurement of potential difference on the semiconductor wafer and the surface-treatment processing thereof, and this results in increased plasma reactor costs and, hence, an increased number of treatment processes.

SUMMARY OF THE INVENTION

The present invention is directed to such a technical background, and one of its objects is to provide a potential difference and current measuring method that enables the DC potential difference on a target object to be measured using a simplified means via a potential difference and current measuring arrangement having a simplified configuration.

Another object of the present invention is to provide a method that enables samples to be efficiently processed while the processes are being monitored using an apparatus having a simplified configuration.

When a light-emitting diode or the like is left in a plasma-exposed atmosphere, the potential difference arising from the resulting flow of charged particles (ions and electrons) from the plasma will create the flow of an electric current into the light-emitting diode and activate it to emit light. The light emission intensity of the light-emitting diode has a constant correlation with the voltage and current of the diode. The present invention utilizes this property.

The present invention is characterized in that, in a method of measuring the potential differences for plasma processing with a plasma processing apparatus that processes a sample by introducing a gas into vacuum chambers and generating a plasma: a light-emitting portion is formed on a measurement sample; the potential difference generated according to the difference in the amount of plasma-incident charged particles is detected; a current flows into said light-emitting portion according to the potential difference that has been generated across said light-emitting portion; the intensity of the light emitted from said light-emitting portion according to the particular level of said current is measured; and the potential difference on said measurement sample according to the particular light intensity is measured.

The present invention is also characterized in that, in a method of measuring the plasma processing potential difference on the object to be plasma-processed by introducing a gas into vacuum chambers and generating a plasma: a light-emitting portion is formed on said object to be plasma-processed; the flow of charged particles from the plasma to the surface of said object is measured as the intensity of the light emitted from said light-emitting portion according to the level of the current flowing thereinto; and the amount of current flowing into said object according to the particular light intensity is measured.

For example, antennas for acquiring charged particles from plasma to the terminals of the light-emitting portion are connected first. These antennas are then installed inside the plasma processing apparatus or on the wafer, and the light emission intensity of the light-emitting portion is measured. It is possible to measure the potential difference between any two positions by establishing the correlation expression between the pre-calculated light emission intensity and voltage-current characteristics of the light-emitting portion and converting the light emission intensity into a voltage, or to measure the plasma current between any two positions by converting the light emission intensity into a current using the above-mentioned expression.

To measure the plasma potential difference, the circuit resistance value of a light-emitting diode needs to be greater than an external circuit resistance including the plasma, or, to measure the plasma current, the circuit resistance value of the light-emitting diode needs to be smaller than the above-mentioned external circuit resistance value. This method requires only a window for measuring light intensity, and does not require lead wires or lead wire lead-in terminals.

In order to fulfill the foregoing objects, a potential difference measuring method based on the present invention uses a potential difference and current measuring arrangement equipped with one pair of conductor antennas, a light-emitting portion connected between the conductor antennas, and an AC voltage bypass element connected in parallel to the light-emitting portion, and a means is provided for arranging/connecting the conductor antennas at/to the potential measuring positions on the object to be measured and for measuring the DC potential differences at these potential measuring positions by detecting the intensity of the resulting light output from the light-emitting portion.

According to the means described above, after the arrangement and connection of the conductor antennas at/to the potential measuring positions on the object to be measured, when DC potential differences exist at these potential measuring positions, the light-emitting portion or the light-emitting diodes will emit light. The DC potential differences at the potential measuring positions can therefore be measured by visually detecting the emitted light intensity from the unit containing the target object (for example, from the exterior of the plasma generating layer) through an optical unit, such as a charge-coupled device (CCD) camera. Thus, it is unnecessary to provide connection lead wires to acquire detection output signals, or a sample mount in which conductor probes for detection are embedded.

In this case, since an AC voltage bypass element (preferably, a capacitor) is connected in parallel to the light-emitting portion, any AC potential differences between potential measuring positions are bypassed by the AC voltage bypass element and only the DC potential differences at the potential measuring positions can be measured.

The present invention also makes it possible to supply a highly efficient sample-processing method that uses a potential difference and current measuring portion having a simplified configuration.

DETAILED DESCRIPTION OF PREFERRED EMBODIMENTS

Embodiments of the present invention will be described with reference to the drawings.

Figure 1:
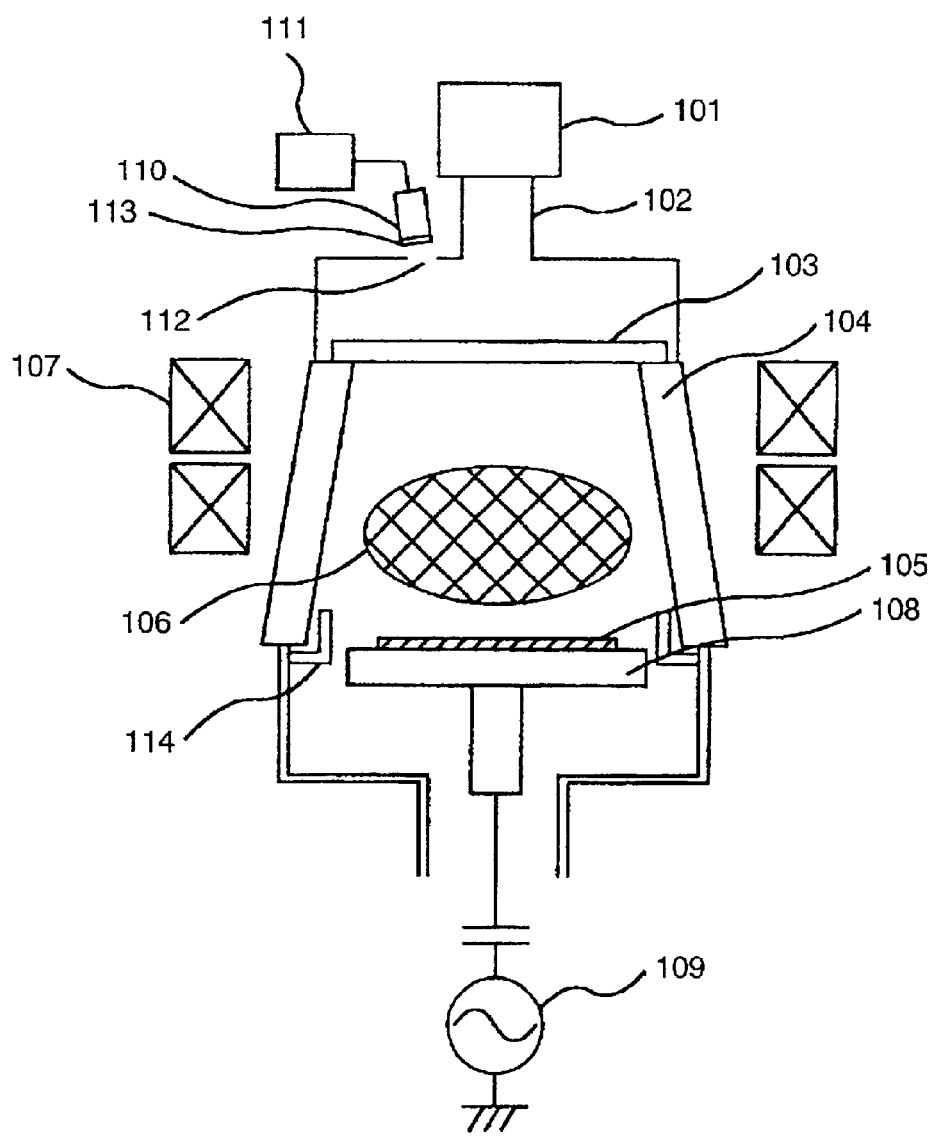
FIG. 1 is a diagram of an ECR etching apparatus.

A diagram of an ECR type of etching apparatus, to which the present invention is applied, is shown in FIG. 1. Microwaves are introduced from microwave power supply 101 into vacuum chamber 104 via waveguide 102 and window 103. The window 103 is made of a material that transmits electromagnetic waves, such as quartz. Around vacuum chamber 104 there are arranged electromagnets 107, and the strength of the magnetic fields generated thereby is set so as to generate a resonance with the frequency of the microwaves. For example, if the frequency is 2.45 GHz, the magnetic field strength is 875 Gauss. Wafer 105 (or plasma potential difference and current measuring unit 200) is mounted on sample mount 108. A high-frequency power supply 109 is connected to sample mount 108 in order to accelerate the flow of ions into the wafer. The earth ring 114 against the high-frequency waves is provided around sample mount 108.

Also, in order to measure the light emission intensity of the light-emitting diodes to be mentioned later, the waveguide has a window 112, through which an image of the wafer is monitored using a CCD (charge-coupled device) camera 110. Data that has been acquired by the camera is processed by personal computer 111. In order to receive the light emitted from the plasma 106, camera 110 has an interference filter 113 adjusted to the light emission wavelength of the light-emitting diodes.

Figure 2:
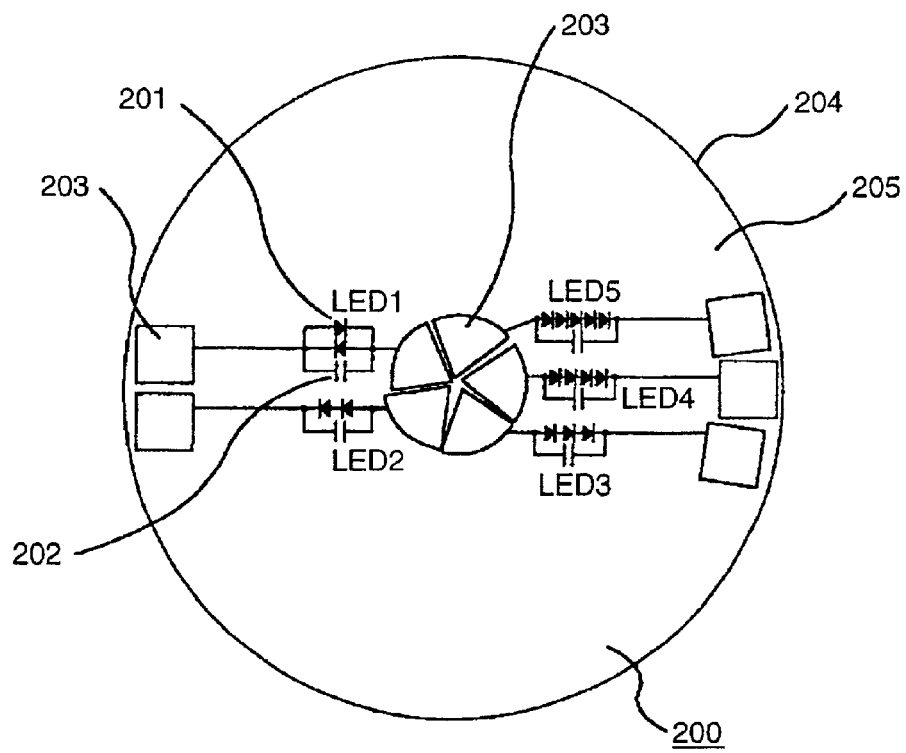
FIG. 2 is a top view of the potential difference and current measuring unit representing an embodiment of the present invention.
Figure 3:
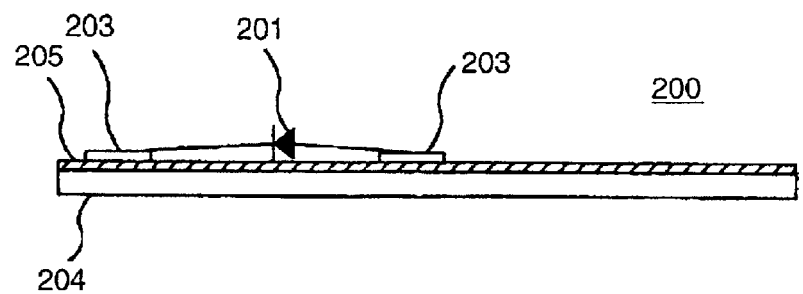
FIG. 3 is a cross-sectional view of the potential difference and current measuring unit of the present invention.

FIG. 2 is a top view of plasma potential difference and current measuring unit 200 (an embodiment of the present invention), and this measuring unit has a potential difference and current measuring device mounted on a measurement sample of similar material and shape as those of the wafer 105 which is to undergo processing. The measuring unit 200 is mounted on the sample mount 108. FIG. 3 is a cross-sectional view of the plasma potential difference and current measuring unit 200.

Plasma potential difference and current measuring unit 200 has an oxide film 205 deposited on a silicon substrate 204, and a light-emitting diode (LED) 201 is mounted on the oxide film. Aluminum antennas 203 are connected at both ends of the LED via insulated conductors. The plasma reactor used for etching ranges from 0.5 to 5.0 mA/cm$^2$ in saturated ion current density. Since the turn-on current (on-emission energizing current) of the LED 201 is only about 1 mA, the surface areas of the conductor antennas can be set to exceed the range from 0.2 to 2.0 cm$^2$. The antenna areas can usually be adjusted according to the particular plasma density.

In this measuring unit, as shown in FIG. 2, there are five groups including one to five light-emitting diodes (LED1 to LED5), respectively, connected in series, and independent antennas are connected at both ends of each LED group. In this way, the starting threshold voltage of light emission from each LED group is varied to improve the measurement accuracy. Each LED group has a parallel-connected capacitor 202 operating as a filter for removing AC voltage components. The appropriate value of the capacitor is about one microfarad when the frequency of high-frequency power supply 109 is 800 kHz. Usually, however, it suffices just to change the value according to the particular frequency. Also, since this example assumes that the potential in the center of the wafer is greater than that developed around the periphery of the wafer, the connection polarity is set so that each diode emits light when potentials are distributed that way. Only in the group where one LED is present, is a reverse polarized diode also connected in parallel. Thus, detection is possible when the potential around the wafer is higher.

Figure 4A:
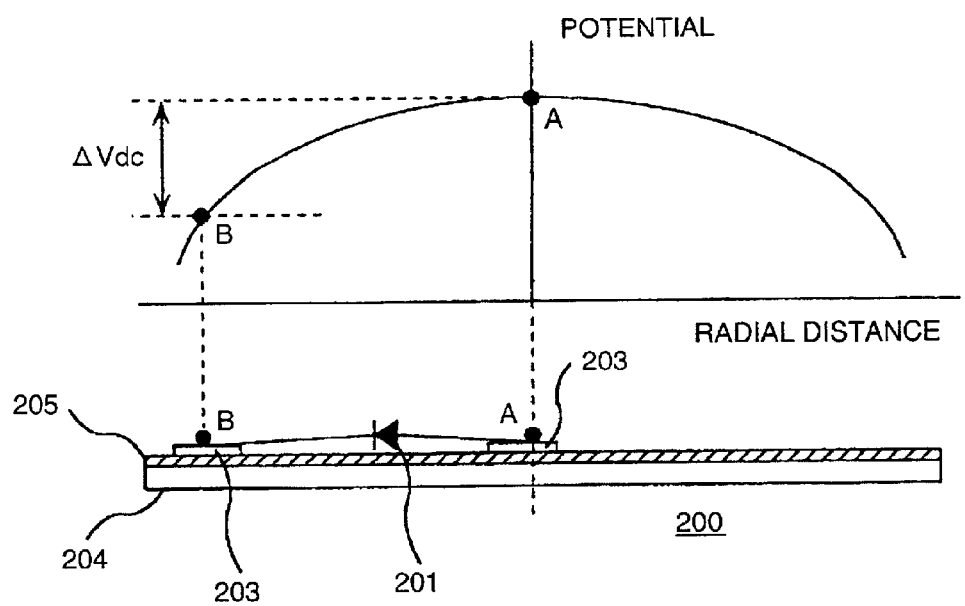
FIG. 4A is a diagram of the potential difference and current measuring unit illustrating the principles of the present invention.
Figure 4B:
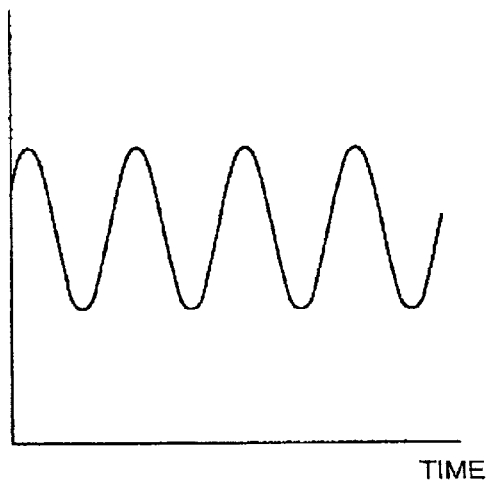
FIG. 4B is a graph showing the variation in potential different with time.

FIG. 4A shows the distribution of the potentials developed on wafer 105 (or plasma potential difference and current measuring unit 200) in the etching apparatus shown in FIG. 1. The nonuniformity of potentials on the wafer is caused by the nonuniformity of the plasma density and/or the nonuniformity in the distribution of currents from high-frequency power supply 109. In FIG. 4A, the potential at the center point A of the wafer is higher than the potential at the edge point B of that wafer by ΔVdc. Also, the high-frequency voltage components of high-frequency power supply 109 overlap on the wafer; and, as shown in FIG. 4B, the potential between points A and B changes with time. Even if ΔVdc is zero, since each LED emits light with the above-mentioned high-frequency components, capacitor 202 is connected in parallel to LED 201 to ensure that only the DC component of ΔVdc is measured. Therefore, when the measuring unit shown in FIG. 2 is installed under plasma processing conditions, the LED will emit light according to ΔVdc.

Figure 5:
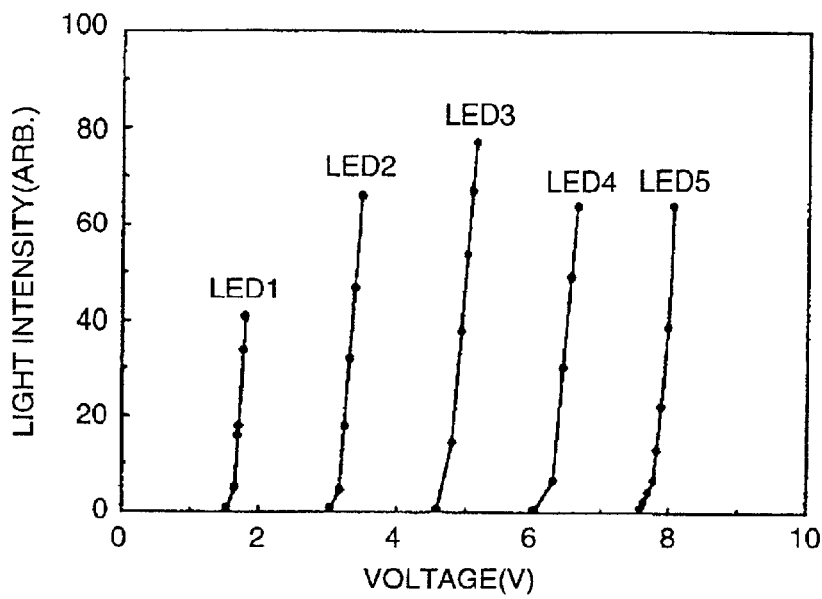
FIG. 5 is a graph showing the relationship between the voltage applied to light-emitting diodes and the intensity of the light emitted from the diodes.

The relationship between the voltage applied to a series-connected LED and its light emission intensity is represented in FIG. 5, wherein LED1 to LED5 are the identification numbers of the series-connected diode groups. These diodes emit red light, and the light-emission starting threshold voltage of one such diode is 1.5 V. When one to five diodes are connected in series in the respective groups, therefore, the respective light-emission threshold voltages are 1.5 V, 3.0 V, 4.5 V, 6.0 V, and 7.5 V.

Figure 6:
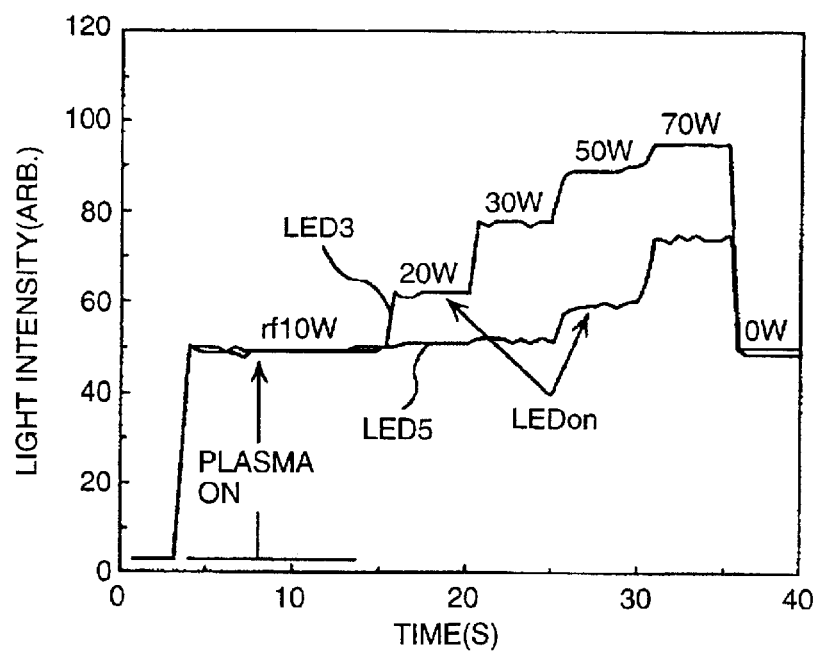
FIG. 6 is a graph of light intensity versus time showing an example of application results produced by the present invention.

FIG. 6 shows the LED light-emission intensity data measurements using camera 110 that were obtained in the case where the plasma potential difference and current measuring unit 200 shown in FIG. 2 was installed in the etching apparatus of FIG. 1. The horizontal axis denotes time, and the output of high-frequency power supply 109 was changed in steps from 10 W to 70 W with time. Light-emission intensity data that was obtained using three connected LEDs, and same data that was obtained using five connected LEDs are shown as examples in FIG. 6. It can be seen from this figure that when the three connected LEDs started emitting light at 20 W, ΔVdc exceeded 4.5 V, and when the five connected LEDs started emitting light at 50 W, ΔVdc exceeded 7.5 V.

Figure 7:
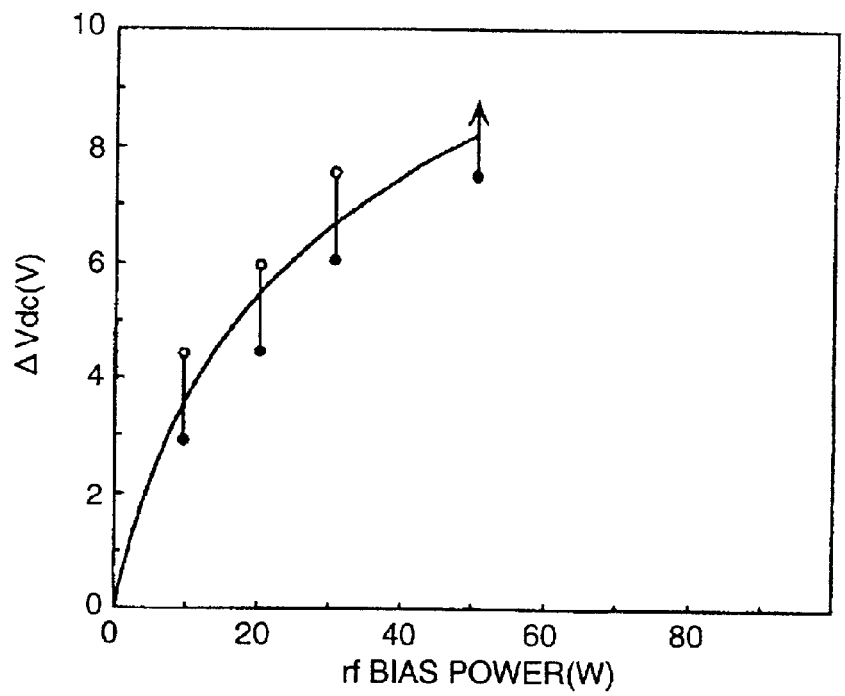
FIG. 7 is a graph of potential difference versus high frequency power showing an example of application results produced by the present invention.

The measurement results on the relationship between high-frequency power and ΔVdc that were obtained using the above-mentioned method are shown in FIG. 7. The gas was a combination of 74-sccm chlorine and 6-sccm oxygen, and the gas pressure was 0.4 Pa. Also, the output of microwave power supply 101 was 400 W. These are etching parameters relating to the poly-silicon used for a semiconductor device.

Since the potential difference (ΔVdc) occurring on the wafer placed in plasma is a quantity related to the insulation breakdown of the gate oxide film on the transistor processed on that wafer, it is important to measure ΔVdc. When an etching apparatus is developed or etching parameters are determined, it is necessary not only that an etching rate and other parameters relating to characteristics be appropriate, but also that the gate oxide film be free from insulation breakdown.

In the case of prior art, it is necessary that, during the measurement of a potential difference using the probe-embedded electrodes described in the examples of known methods, an apparatus be designed or etching parameters be determined so as to minimize the potential difference, and then the electrodes can be replaced with the normal sample mount to etch the sample.

In accordance with the present invention, since the unit for measuring ΔVdc, namely, the plasma potential difference and current measuring unit 200 has the same shape as that of a wafer, it is possible to measure ΔVdc without performing any modifications on the etching apparatus, and to etch semiconductor devices just by changing wafers after determining the parameters for a sufficiently small value of ΔVdc. In other words, it is possible to reduce the processing time and to analyze etching characteristics, and measure the potential difference inside the wafer, with exactly the same apparatus configuration.

In the embodiment described above, although the antennas at both ends of each LED group are arranged in the center of and around the wafer, these antennas can be moved according to the desired potential difference measurement position on the wafer.

Also, the light emission intensity detected by the camera depends on factors such as the camera-to-LED distance and the light transmittance of the window material. The absolute potential difference value can therefore be obtained by measuring the above-mentioned distance and transmittance and calibrating the detection portion of the camera. Even if the calibration is not performed, the relative magnitude of the potential difference inside the wafer can be judged from the light emission intensity.

Since a distribution curve of the potentials developed on the wafer does not always have a humped middle, as shown in FIG. 4A, the polarity of the potentials can be judged by mounting one set of forward- and reverse-polarized LEDs in connected form on the wafer.

In FIG. 2, LEDs 201 and capacitors 202 can be shielded with polyimide or the like, as required, and thus the LEDs and the capacitors can be protected from plasma-induced damage.

The potentials on the wafer can also be measured together with their AC components by removing capacitors 202. The number of LEDs to be connected in series in each group can be adjusted (or blue diodes and other diodes different in light emission threshold voltage can be used) according to the particular magnitude of ΔVdc.

Figure 8A:
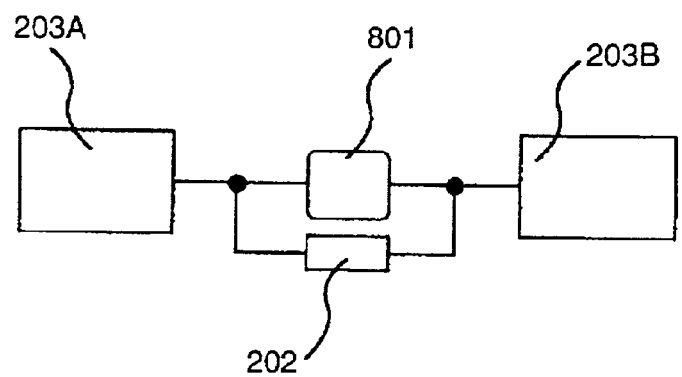
FIGS. 8A and 8B are block diagrams of embodiments of the potential difference and current measuring unit of the present invention.
Figure 8B:
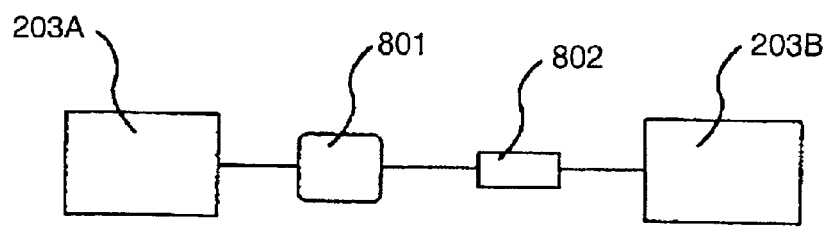

Camera 110 for measuring the light emission intensity can be installed inside the vacuum chamber 104 provided with the appropriate electromagnetic interference countermeasures, and the light-receiving portion can be equipped with an optical fiber. In FIG. 8A, light-emitting circuit 801 is inserted between antennas 203A and 203B, and capacitor 202 is connected in parallel to light-emitting circuit 801 to remove AC components. When a potential difference occurs between antennas 203A and 203B, since the light-emitting circuit emits light according to the particular potential difference, this value can be identified by closely observing the quantity of light which has been emitted. To remove AC components, coil 802 can be connected in series to light-emitting circuit 801, as seen in FIG. 8B, instead of connecting capacitor 202 in parallel to light-emitting circuit 801. The light-emitting circuit here refers to a circuit that includes light-emitting diodes 201 or so-called miniature lamps whose resistance values change according to the voltage applied across the circuit, or refers to a laser, such as a semiconductor laser, that includes light-emitting elements. Various embodiments of this light-emitting circuit will be described later. Although light-emitting circuit 801 that includes light-emitting elements is described here, a unit for generating sound waves or electromagnetic waves (such as ultraviolet rays, infrared rays, or X-rays) that change in intensity according to the voltage applied across the circuit can be used, instead of light-emitting elements. When such a unit is used, however, it is, of course, necessary to use a sensor or filter as well, instead of camera 110 or interference filter 113, that can detect those sound wave signals or electromagnetic wave signals. It is important to provide a means for generating some type of physical quantity according to either the voltage applied across the circuit, or the current corresponding to the voltage, and a means for detecting the physical quantity at a position far from the means mentioned above.

Figure 9:
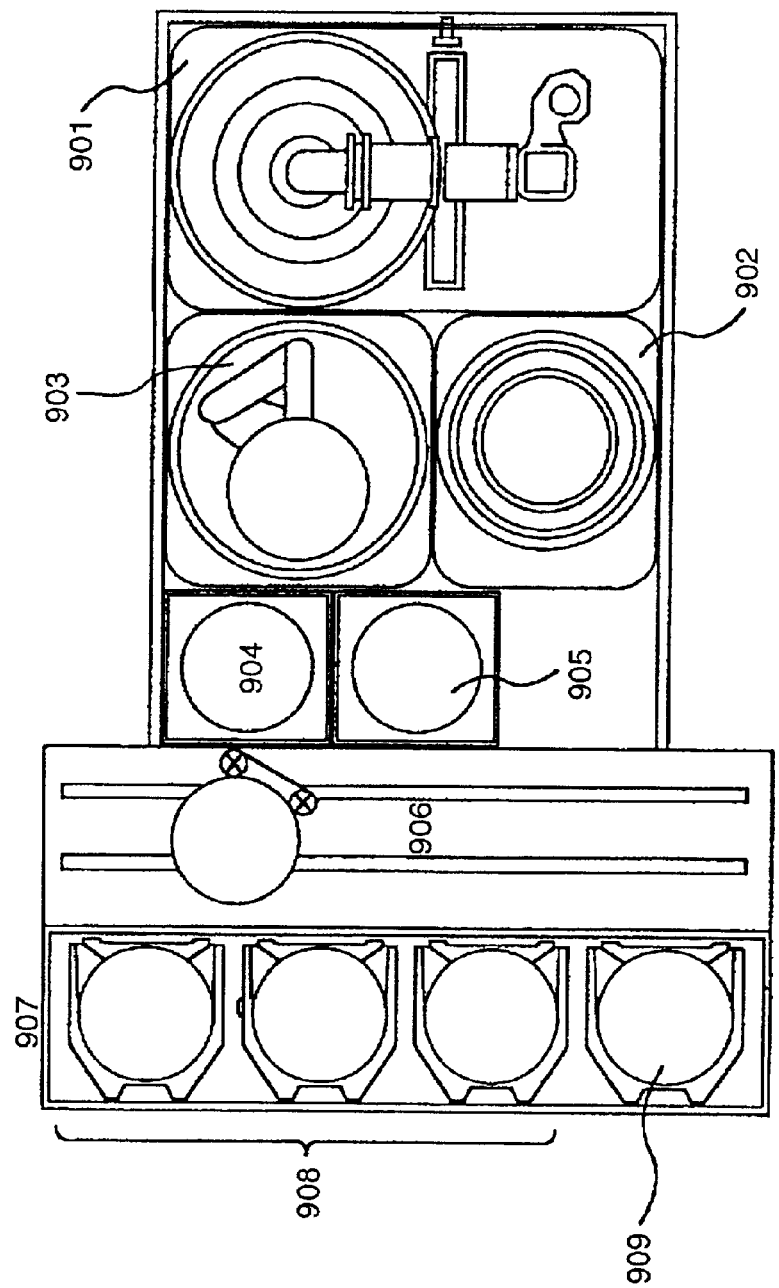
FIG. 9 is a top view of semiconductor processing equipment which uses the potential difference and current measuring unit of the present invention.

Next, a method of using plasma potential difference and current measuring unit 200 to manufacture semiconductors will be described. An example of semiconductor manufacturing equipment is shown in FIG. 9. This equipment includes, more specifically, an etching apparatus, a CVD apparatus, etc.

The semiconductor manufacturing equipment shown in FIG. 9 has processing chamber 901, a second processing chamber 902, a wafer transport robot 903, a loading lock chamber 904, an unloading lock chamber 905, a loader 906, and a stocker 907. Stocker 907 contains cassettes 908 and a dummy cassette 909. When a wafer is processed in processing chamber 901, the wafer 105 within cassette 908 under almost atmospheric conditions is transported to the loading lock chamber 904, which is also under almost atmospheric conditions, by loader 906, and then the loading lock chamber is closed. After the loading lock chamber 904 has been decompressed to a suitable pressure, wafer transport robot 903 transports wafer 105 to processing chamber 901, where the wafer is then provided with appropriate processing. After being processed, wafer 105 is transported to the unloading lock chamber 905 by the wafer transport robot 903. After the internal pressure of the unloading lock chamber 905 has been increased nearly to atmospheric pressure, wafer 105 is returned to cassette 908 by loader 906. Such processes are usually repeated.

Figure 10:
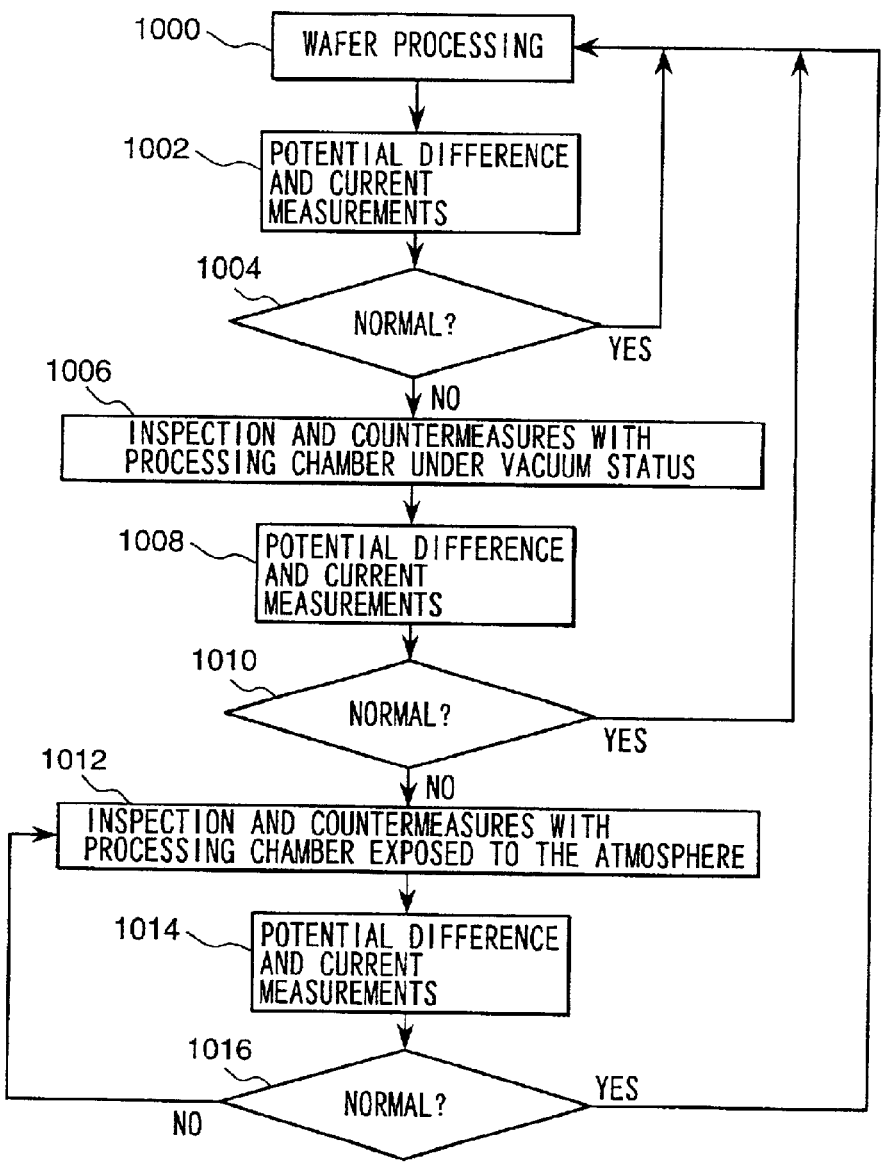
FIG. 10 is a flowchart of a process intended to improve productivity by applying the potential difference and current measuring unit of the present invention to semiconductor processing.

Next, a method of using plasma potential difference and current measuring unit 200 to process wafers will be described with reference to FIG. 10. Wafers 105 usually undergo processing in processing chambers 901 and 902 (S1000). When processing parameters are checked periodically or non-periodically, the plasma potential difference and current measuring unit 200, that has been placed in dummy cassette 909 beforehand, is transported to the processing chambers, where the processing parameters can then be checked (S1002). That is to say, when the processing parameters are to be checked, the plasma potential difference and current measuring unit 200 that has been placed in dummy cassette 909 beforehand is transported to the loading lock chamber 904 by loader 906, and then it is transported to the processing chamber 901 by wafer transport robot 903. After this, the plasma potential difference and current measuring unit 200 is subjected to processing conditions with predetermined parameters and the light emission status at this time is monitored to confirm the presence/absence of an abnormality and to detect its level (S1004).

When no abnormality is detected, the potential difference and current measuring unit 200 is removed using wafer transport robot 903, and is then placed in unloading lock chamber 905, from which it is returned to the dummy cassette 909 by loader 906 to restart semiconductor processing (S1000).

If an abnormality is detected, the processing chambers are maintained in a vacuum state as long as possible and the processing apparatus is checked and provided with countermeasures (S1006). After the countermeasures have been undertaken, the plasma potential difference and current measuring unit 200 is subjected to processing conditions with predetermined parameters once again and the light emission status is monitored (S1008) to confirm the presence/absence of an abnormality and detect its level (S1010).

At this time, when no abnormality is detected, the potential difference and current measuring unit 200 is removed using wafer transport robot 903, and it is then placed in the unloading lock chamber 905, from which it is returned to the dummy cassette 909 by loader 906 to restart semiconductor processing (S1000). If an abnormality is detected again at this time, the potential difference and current measuring unit 200 is removed using wafer transport robot 903, and it is then placed in the unloading lock chamber 905, from which it is returned to the dummy cassette 909 by loader 906. After this, the processing chambers are exposed to the atmosphere and necessary maintenance takes place (S1012). The necessary maintenance here refers more specifically to replacement of consumable parts and removal of sticking film from the various sections of the processing chambers by use of substances such as an organic solvent.

After proper maintenance has been performed, the processing chambers are placed in a vacuum state once again to enable semiconductor processing. At this time, semiconductor processing is not started immediately. Instead, it is started only after it has been confirmed that processing chamber 901 has returned to normal is using the potential difference and current measuring unit 200 (S1014 to S1016). If an abnormality is detected during this process, it is determined that the processing chamber 901 or the entire semiconductor manufacturing equipment requires rechecking and that the maintenance processes described above are to be performed again, and/or more extensive maintenance processes are to be performed.

Processing parameters relating to the potential difference and current measuring unit 200 of the present invention do not always need to match the semiconductor processing parameters. Given the same parameters, whether the parameters are being properly maintained is to be judged. However, the use of the parameters enables easy detection of an abnormality, although these parameters differ from actual processing parameters, and makes it possible to estimate beforehand any abnormal states that slightly change with the progress of time. Since these parameters differ from actual processing parameters, semiconductor processing does not always need to be stopped, even if an abnormality is detected. If an abnormality is detected under conditions using these parameters, however, after semiconductor processing has been restarted, the equipment status monitoring time is to be made shorter than usual, by using the potential difference and current measuring unit of the present invention once again. This maintains the equipment availability and prevents processed wafers from being wasted.

In the above-described embodiment, although atmospheric cassettes are used for descriptive reasons, vacuum cassettes can also be used instead.

Figure 11:
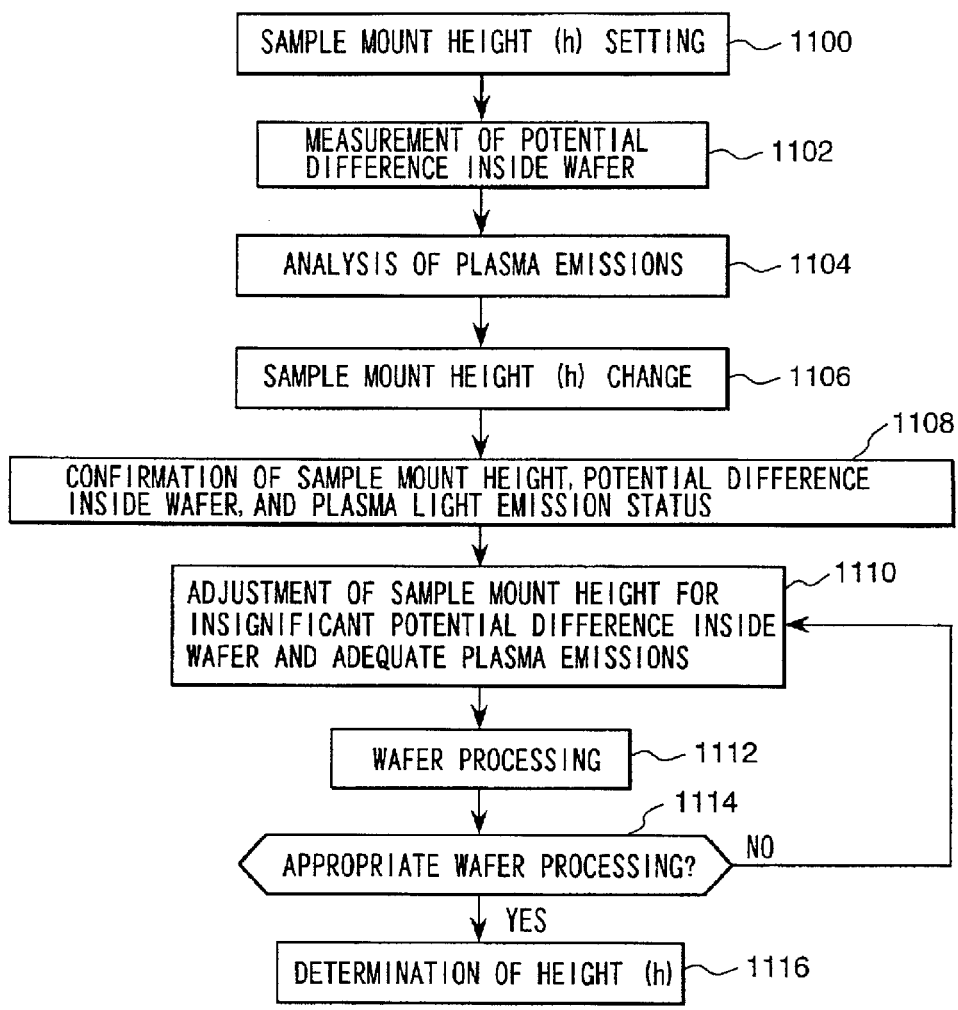
FIG. 11 is a flowchart of a process intended to apply the potential difference and current measuring unit of the present invention to the optimization of semiconductor processing equipment.

Next, a method of using the potential difference and current measuring unit 200 to develop processing unit 901 or etching processes will be described with reference to FIG. 11. In this case, the potential difference and current measuring unit is to be inserted into the semiconductor manufacturing equipment to be developed, for example, the etching apparatus shown in FIG. 1.

For example, to optimize the height of the sample mount 108 for reduced potential difference inside the wafer, it is necessary first to keep constant the output power of the microwave power supply for generating plasma, the output power of the high-frequency power supply for applying a bias voltage to the wafer, the internal pressures of the processing chambers, the flow rate of the gas to be introduced into the processing chambers, and other parameters, and then to mount potential difference and current measuring unit 200 on the sample mount 108 and observe light emission status. Next, only the height of the sample mount is to be changed, and the light emission status is to be observed again (S1100).

Parameters that generate an insignificant potential difference inside the wafer can be found by repeating the above experiments and examining the relationship between the height of the sample mount and light emission status.

This method can be used merely by inserting the potential difference and current measuring unit into the processing chamber, instead of the wafer 105, and does not require special electrodes. Also, since this method enables the quantity of light (namely, the potential difference) to be immediately determined, actual processing can be executed using wafer 105 before or after measurement, and spectral analyses on the status of light emission from the plasma 106 can be easily conducted during, before, or after measurement. That is to say, the height of sample mount 108, the potential difference inside the wafer, the plasma status at the particular time, and wafer processing results can be obtained for one set of parameters; and, as a result, the configuration of the equipment can be optimized in various terms (S1102 to S1108). Although the height of the sample mount 108 is taken as an example in the description given above, this method is also valid for optimizing other factors, such as the size of the sample mount, the position of the gas introducing port, and the size and position of the earth ring 114.

In addition, this method is valid for optimizing not only the hardware-like configuration of the equipment, but also the type of processing gas, the pressure, the magnetic fields, the output power and frequency of the microwave power supply, the output power and frequency of the high-frequency power supply, and various other processing parameters (S1110 to S1116).

The etching apparatus shown in FIG. 1 is an example of the reaction chamber 901.

Figure 12:
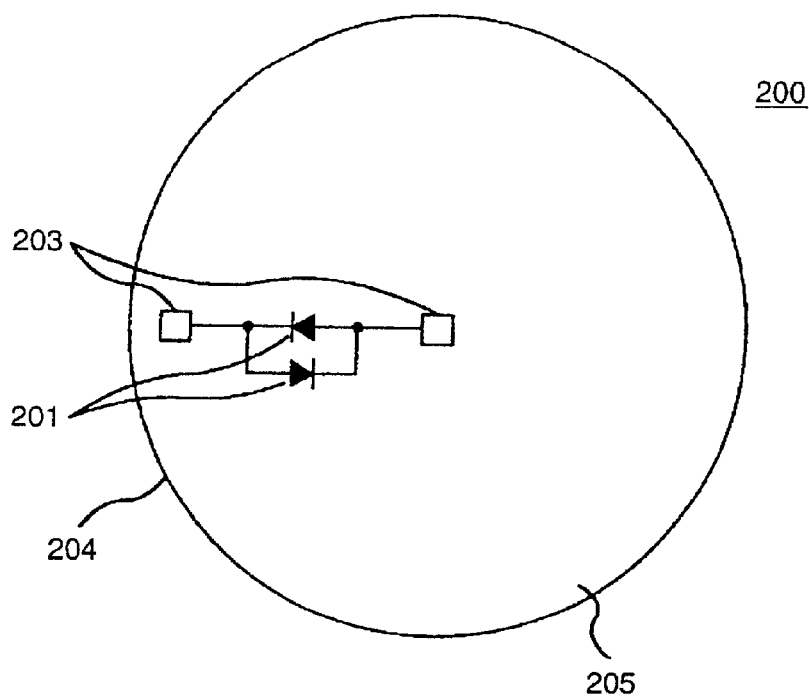
FIG. 12 is a schematic diagram of a potential difference measuring unit, based on the present invention, which does not have a capacitor.

FIG. 12 is a schematic diagram of the potential difference and current measuring unit 200 according to another embodiment of the present invention for a case in which a bias voltage is not applied. The measuring unit configuration in FIG. 12 differs from that of FIG. 2 in that capacitor 202 for removing AC components is not provided. When no bias voltage is applied, AC components can be ignored, and configurations without capacitor 202 usually pose no problem. As a matter of fact, for a CVD or ashing unit, there are occasions when no bias voltage is applied, even during plasma processing.

Figure 13:
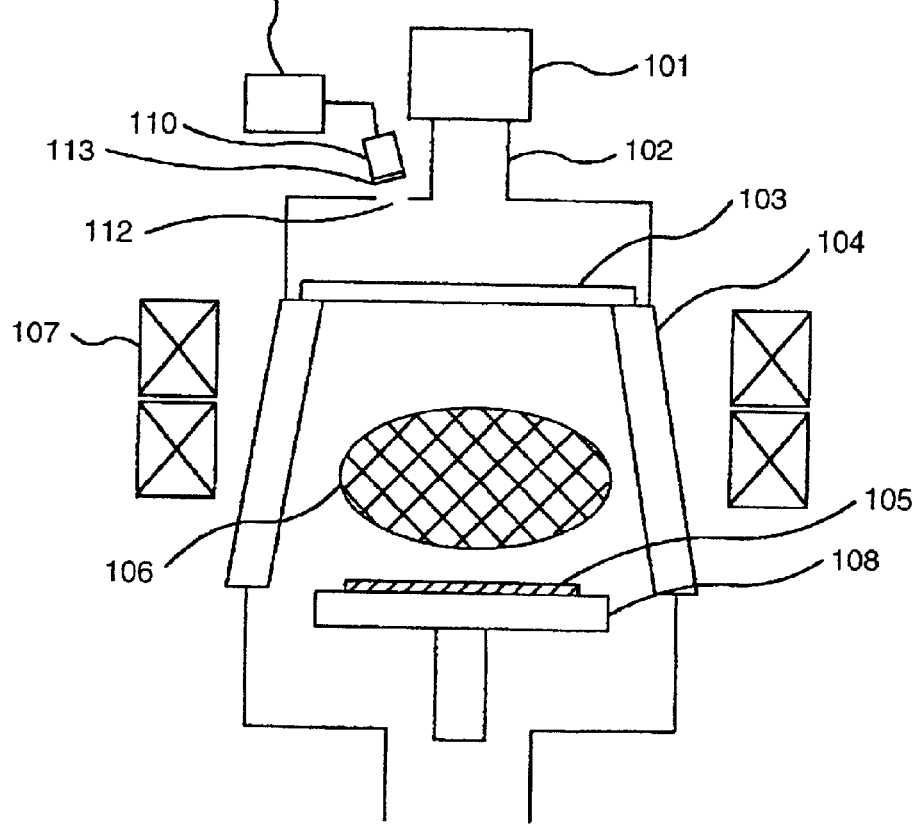
FIG. 13 is a diagram of an ashing apparatus.

An example of an ashing unit not requiring the application of a bias is shown in FIG. 13. Although the configuration shown in FIG. 13 is similar to that of FIG. 1, high-frequency power supply 109 and earth ring 114 are absent in the configuration shown in FIG. 13. The type of gas used to remove resist is an argon gas, an oxygen gas, or the like. When the potential difference and current measuring unit shown in FIG. 12 is actually used, this measuring unit is introduced into a unit, such as the ashing unit mentioned above.

Figure 14:
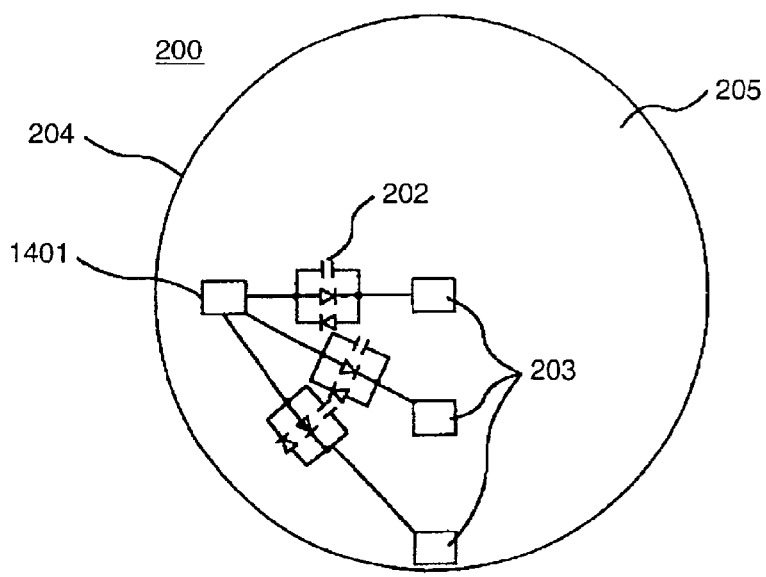
FIG. 14 is a schematic diagram of a potential difference measuring unit based on the present invention.

In the potential difference and current measuring unit 200 of the present invention, one of the two antennas can also be routed through a circuit substrate. A modified version of the potential difference and current measuring unit shown in FIG. 2 or FIG. 12 is shown in FIG. 14. In this case, one terminal of light-emitting diode (1401) is characterized in that it is routed through substrate 204. In general semiconductor manufacturing processes, the potential of the gate with respect to that of the substrate is usually picked up as a problem. In the configuration described above, however, the voltages of the substrate and gate can be measured. Also, in this unit configuration, antenna 203, which is not routed through the substrate, is installed in three places which are at different distances from the center of the wafer. Thus, the potential difference between antenna 203 and silicon substrate 204 can be detected.

Figure 15A:
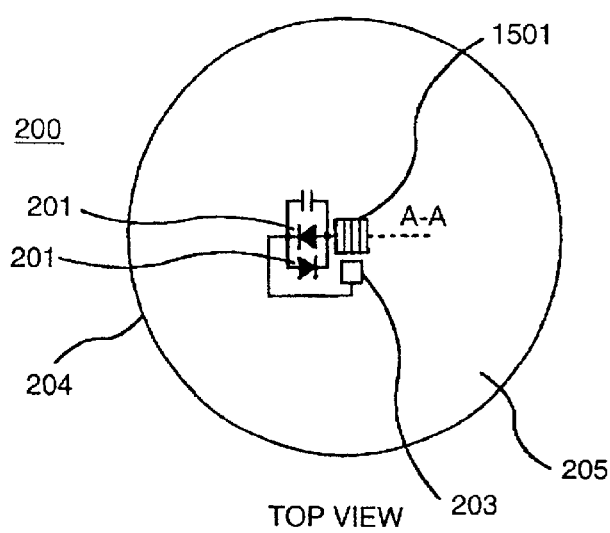
FIG. 15A is a schematic diagram of a potential difference measuring unit based on the present invention.
Figure 15B:
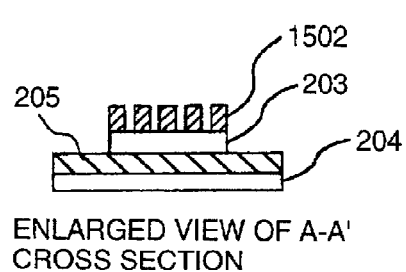
FIG. 15B is a sectional view taken along line A—A in FIG. 15A.

In addition, a comb-shaped antenna can also be used instead. The potential difference and current measuring member shown in FIGS. 15A and 15B is composed of two LEDs 201 connected in parallel in opposite directions between comb-shaped antenna 1501 and antenna 203, and a capacitor 202 is connected in parallel to the LEDs. The measuring member shown in FIGS. 15A and 15B is located on and connected to insulating film 205, with which the surface of silicon substrate 204 is covered. In this case, comb-shaped antenna 1501 is formed using resist 1502 processed in line-and-space form on conductor antenna 203 positioned on insulating film 205. The pattern of the line-and-space form on resist 1502 is formed by lithography during semiconductor manufacturing processes, and the sizes of the lines and spaces are very small (several microns or less). Modification of antenna 203 into structure such as that of comb-shaped antenna 1501 enables measurement of the DC potential difference in the microstructure due to a phenomenon generally called "electron shading". Since the flow of ions into the silicon substrate 204 under a plasma state is accelerated, these ions enter the silicon substrate 204 almost vertically. In the meantime, electrons, because of their small mass, are great in random-oriented velocity due to heat, and, therefore, they flow from random directions to the silicon substrate 204.

For this reason, when resist 1502 with a microstructured pattern consisting of very small grooves and holes less than several microns in size is present on silicon substrate 204, although a large majority of ions arrive at the bottom of the microstructured pattern, a large majority of electrons cannot reach the bottom. As a result, the bottom of its microstructured pattern is charged positively and the walls of its microstructured pattern are charged negatively, and this phenomenon is called "electron shading". During semiconductor device processing, the bottom of the microstructured pattern is usually connected to the gate oxide film, with the result that, since the gate is charged to cause insulation breakdown, the magnitude of the electron shading needs to be measured.

The comb-shaped antenna 1501 shown in FIGS. 15A and 15B has its silicon substrate 204 charged positively by electron shading, and, thereby, a DC potential difference occurs between comb-shaped antenna 1501 and the antenna 203. One of two LEDs 201, therefore, emits light and the electron shading level can be measured from the intensity of the light. During the measurement of the electron shading level, it is preferable that the comb-shaped antenna 1501 and antenna 203 connected between two LEDs 201 should be arranged close to one another so as to avoid the overlapping of DC potential differences between positions. Also, measurements under the status that electron shading and the DC potential difference on the surface of silicon substrate 204 overlap can be performed by spacing the comb-shaped antenna 1501 and the antenna 203.

The value of the current flowing into LEDs 201 can be obtained by arranging the comb-shaped antenna 1501 and planar antenna 203 close to one another and examining the intensity of the light emitted from LEDs 201. The value of the current flowing into LEDs 201 is a quantity determined by the structure of the comb-shaped antenna 1501 and the ion current density of plasma 106. Since the structure of the comb-shaped antenna 1501 is known, the ion current density can be calculated by examining the amount of light emitted within this measuring unit.

If antenna 203, after being made thicker than antenna 1501, is exposed to plasma and both antennas 203 and 1501 are etched, the light emitted from LEDs 201 can be observed while the antenna 1501 remains. Once the antenna 1501 has been etched, however, the current concentration area will decrease and LEDs 201 will stop emitting light. The etching rate can therefore be measured from the light emission duration of the LEDs 201 and the thickness of the antenna 1501. Modification of the pattern on resist 1502 enables the measurement of an etching rate dependent on the new pattern, for example, a resist pattern with a new groove width or with a plurality of holes.

Next, a method of improving the uniformity of the internal etching rates for the wafer surface by use of this measuring unit will be described. During the development of an etching apparatus or the determination of etching parameters, the uniformity of etching rates is required to satisfy predetermined standards for the entire wafer surface. Although conventional methods usually involve the use of interference to measure etching rates immediately, it is very difficult to observe the rates in a plurality of sections immediately at the same time for reasons such as the limited installation position for a spectroscope. Also, when complex patterns exist, simultaneous observation of etching rates is not easy, since it requires sophisticated calculation of diffraction with high accuracy. Unlike such conventional methods, the method described below is a very simple technique, since it only requires that the above-mentioned measuring unit be installed in multiple places on the wafer and that the light emitted from light-emitting circuit 801 be observed during etching.

The requirement that the uniformity of flat areas in etching rate over the entire wafer surface should be high refers to the requirement that fluctuations in the light emission duration of light-emitting circuit 801 should be insignificant. Accordingly, in the plasma etching apparatus of FIG. 1, when fluctuations in the light emission duration of light-emitting circuit 801 are measured with each etching process under different settings of parameters, such as the flow rate of the gas to be introduced during etching, if the measured fluctuations are insignificant, this means that the etching rates for the flat areas are uniform over the entire wafer surface.

An antenna with patterns can be easily constructed by resting a micropatterned insulating material on the conductor portion of the antenna. This insulating material may be, for example, the J5022-11 capillary plate manufactured by Hamamatsu Photonix Corp. This capillary plate has a plurality of holes 10 microns across and 400 microns deep. For actual semiconductors, problems usually occur when areas about one micron or less in size undergo processing. However, according to Reference [1] below, it is known that when the sizes, of the patterns are sufficiently smaller than typical sizes such as an average free stroke and a sheathing thickness, provided that the patterns are analogous, equality in absolute size is not mandatory. That is to say, the use of the above-mentioned capillary plate or its processed or similar product enables the situation of the order of one micron to be easily simulated without using lithography or the like.

Reference [1]: N, Mise et al., "Proceedings of the 5th International Symposium on Plasma Process-Induced Damage", p. 46, 2000.

Figure 16A:
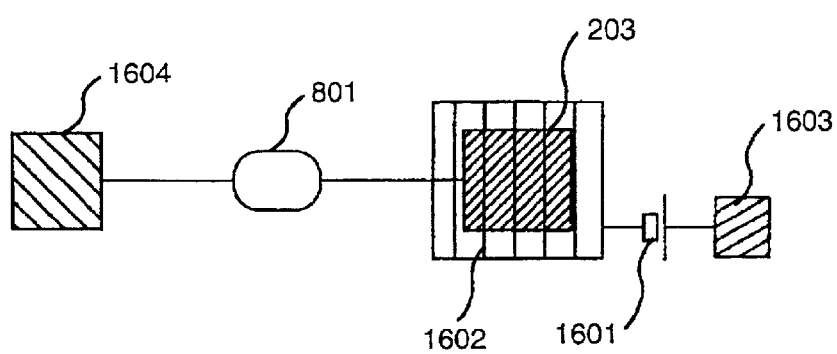
FIG. 16A is a diagram of a potential difference measuring unit based on the present invention.
Figure 16B:
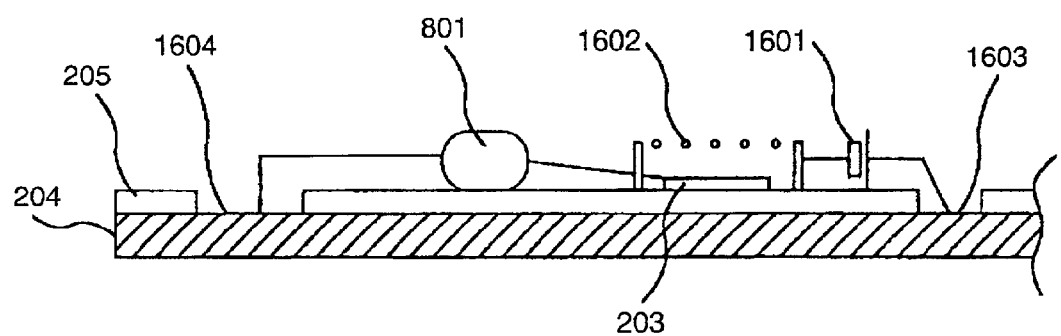
FIG. 16B is a cross-sectional view of the potential difference measuring unit of FIG. 16A.

Next, energy control based on the present invention will be described with reference to FIGS. 16A and 16B. A unit that has meshwork 1602 with a battery 1601 connected to the front of the antenna 203 and which measures the energy of the charged particles entering the antenna, is shown as an embodiment in FIGS. 16A and 16B. A top view of the LED mounted on the unit is shown as FIG. 16A, and a longitudinal section of the LED is shown as FIG. 16B. The battery is connected via hole 1603 of insulating film 205 to silicon substrate 204. The other terminal of the element 801 is also connected to the substrate 204 through hole 1604. When a voltage is applied to meshwork 1602, a repulsive force is given to ions and electrons according to the particular direction and magnitude of the application; and, as a result, only ions whose energy is greater than the applied voltage arrive at antenna 203. Thus, the number of charged particles having a predetermined energy level can be measured from the intensity of the emitted light and the voltage of battery 1601. In the arrangement of FIG. 16A, the distribution of energy can also be measured by installing multiple antennas equipped with batteries 1602 of different voltages.

Figure 17:
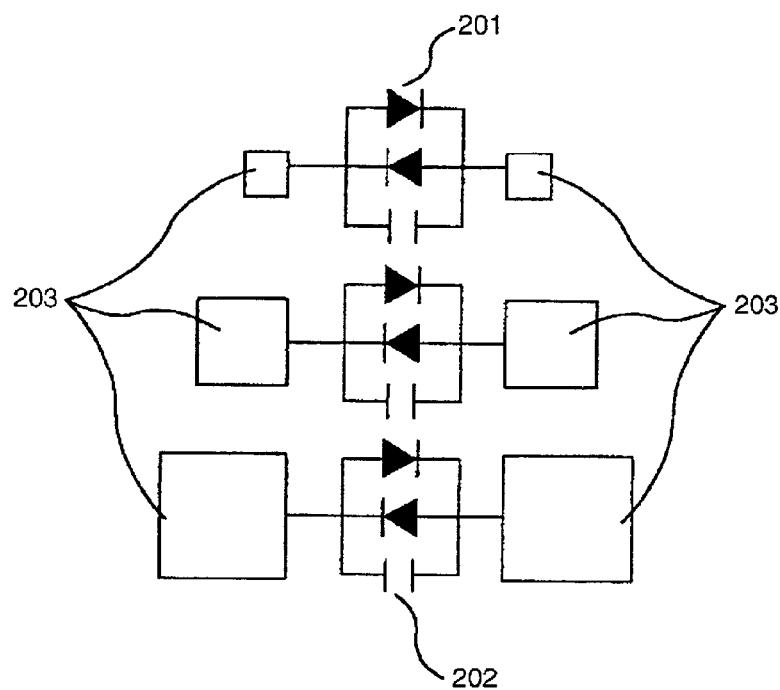
FIG. 17 is a diagram of a potential difference measuring unit based on the present invention.

Next, another embodiment of the present invention will be described with reference to FIG. 17. This figure shows an example of measurement under different surface area settings of antenna 203. In accordance with this measuring method, a sufficient current for activating the LED is required for the measurement of its light emission intensity. The upper limit of the current is a value determined by the antenna area and the density of the plasma. Even when a sufficient current is supplied, if the potential difference across the LED is too low, its light emission intensity is reduced by being limited according to the applied voltage. Whether the light emission intensity of the LED is limited by the voltage or by the current is not univocally determined since the above depends on the current-voltage characteristics of the LED, the magnitude of the potential difference on the wafer, the size of the antenna, the density of the plasma, and other factors. Although the surface area of the antenna needs to be adjusted to find the region where the light emission intensity can be measured, a wide range of currents can be measured at the same time by providing beforehand, as shown in FIG. 17, a plurality of LEDs 201 connected to antennas 203 of different surface areas.

Figure 18A:
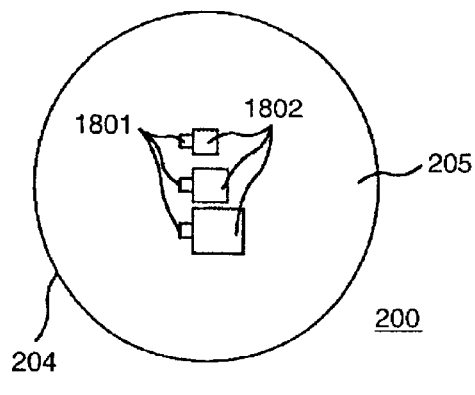
FIG. 18A is a schematic diagram of a potential difference measuring unit based on the present invention.
Figure 18B:
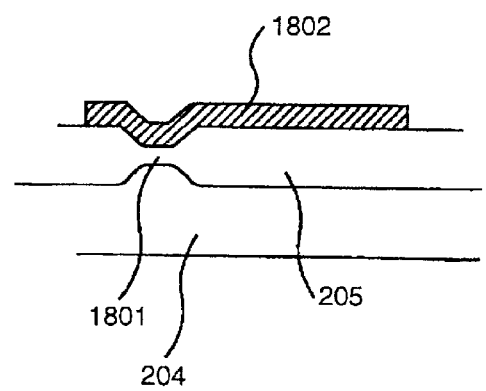
FIG. 18B is a partial sectional view of the potential difference measuring unit of FIG. 18A.

FIG. 18A is a diagram of an on-wafer potential difference measuring unit 200, which represents another embodiment of the present invention. FIGS. 18A and 18B are an enlarged top view and enlarged longitudinal section of this measuring unit. In this embodiment, measuring unit 200 uses thin oxide films as its light-emitting elements. On silicon substrate 204 there is deposited an insulating layer 205, and thin gate oxide films 1801 are provided as part thereof. Antenna 1802, made of poly-silicon or the like, is connected to gate oxide films 1801. The thin oxide films emit light with a sufficient supply of current and can therefore be used similarly to LEDs 201. Since this unit configuration is close to the configuration of a more practical semiconductor wafer processing apparatus, more accurate data measurements can also be obtained.

In the configuration of FIG. 18A, a plurality of light-emitting elements different in antenna surface area are arranged on a wafer. Although only one set of light-emitting elements are shown in the figure, it is possible to arrange multiple sets over the entire wafer surface and measure the distribution of energy. Although it is intended to measure the potential difference between antenna 1802 and silicon substrate 204, this configuration can also be varied to measure the potential differences between any other two positions.

In addition, since the LEDs are made of silicon, not a compound semiconductor, they do not pose problems associated with pollution. Furthermore, during the manufacture of semiconductor devices using a silicon substrate, light-emitting circuit 801 can be formed in, for example, a scribe area or an area not to be used as the semiconductor device at the edge of a wafer, by forming LEDs by use of silicon. The formation of a light-emitting circuit 801 in such areas is, in turn, effective for avoiding a decrease in the number of semiconductor devices which can be obtained from one wafer. Furthermore, the use of this wafer makes it possible to measure the potential difference on the wafer surface under a plasma-exposed status and the degree of damage of the gate oxide film while creating devices. In short, it is possible to evaluate the status of the plasma apparatus and the processing parameters immediately and to estimate a device manufacturing yield.

Figure 19:
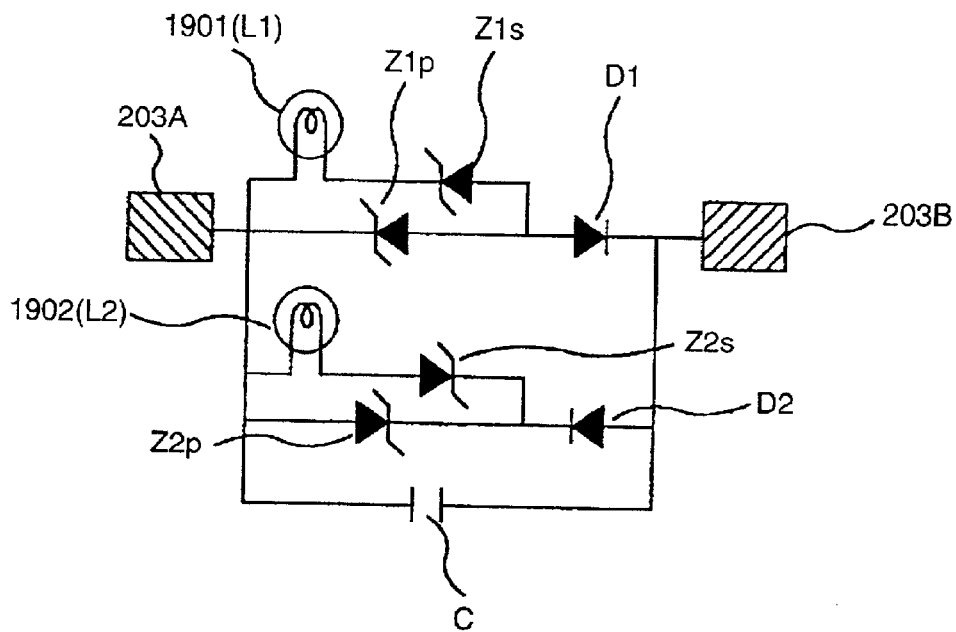
FIG. 19 is a schematic diagram of a potential difference measuring unit based on the present invention.

Next, an embodiment of light-emitting circuit 801 is shown in FIG. 19. In this embodiment, two circuits are connected in parallel between antennas 203A and 203B. The first circuit consists of directly connected light-emitting element 1901 and Zener diode Z1s, another Zener diode Z1p connected in parallel to the 1901—Z1s connection, and diode D1 connected to diode Z1p. The diodes Z1s and the Z1p are polarized in a forward direction, and the diode D1 is polarized in the reverse direction to that of the diode Z1s. The voltage at which a current abruptly begins to flow when a reverse voltage is applied to the Zener diodes is taken as VZ. In this case, Zener diodes Z1s and Z1p are selected so that the absolute threshold voltage VZ1p of the Zener diode Z1p is greater than the absolute threshold voltage VZ1s of the Zener diode Z1s. The second circuit, which consists of the same elements as those of the first circuit, has all its polarized components reversed with respect to the polarized components of the first circuit. In this case as well, Zener diodes Z2s and Z2p are selected so that the absolute threshold voltage value VZ2p of the Zener diode Z2p is greater than the absolute threshold voltage value VZ2s of the Zener diode Z2s. Light-emitting element L1 is an element not having polarity, and L1 is, for example, an element that emits light when activated by the current flowing into a filament made of tungsten.

The conditions where light-emitting element L1 emits light under the light-emitting circuit composition shown in FIG. 19 are described below. Since L1 and D1 are connected in series, it can be seen that at least if $\Delta V = V_A - V_B > 0$ holds, L1 will emit light. However, if the potential difference $\Delta V$ between A and B is smaller than the threshold value of diode D1, namely, if $\Delta V < VD1$, no current flows into L1 because of the effects of diode D1, and this also applies in the case of $\Delta V < VD1 + VZ1s$, even when the potential difference increases. The reason why no current flows into L1 is that Zener diode Z1s does not yield. When the potential difference further increases (ΔV>VD1+VZ1s), Zener diode Z1s yields and a current begins to flow into L1. When the potential difference ΔV increases more significantly (namely, ΔV>VD1+VZ1p), Zener diode Z1p also yields. Therefore, even when the potential difference ΔV increases in the range of ΔV>VD1+VZ1p, the voltage between L1 and Z1s is maintained at a constant value of VD1+VZ1p. This means that Zener diode Z1p protects the circuit by preventing an overvoltage from being applied across light-emitting element L1 or an overcurrent from flowing into L1. Accordingly, ΔV and the light emission intensity of L1 directly vary when VD1+VZ1p<ΔV<VD1+VZ2p. When ΔV<VD1+VZ2p, however, the light emission intensity is kept constant, irrespective of ΔV.

When a reverse voltage is applied, only light-emitting element L2 emits light and L1 and L2 do not emit light simultaneously.

Consider a case in which, more specifically, the HZ6A1 Zener diodes, manufactured by Hitachi, Ltd., are used as Zener diodes Z1s and Z2s, the HZ7A1 Zener diodes, manufactured by Hitachi, Ltd., are used as Zener diodes Z1p and Z2p, and the HSK110 diodes, manufactured by Hitachi, Ltd., are used as diodes D1 and D2. According to the Hitachi Databook issued in September 1992, the yield voltages of the HZ6A1 and HZ7A1 diodes are 5.2 V and −6.3 V, respectively, and the threshold voltage value of the HSK110 is 0.8 V. At this time, when the potential VA of the antenna A becomes 6.0 V higher than the potential VB of the antenna B, the light-emitting element L1 emits light. When the difference between VA and VB is smaller than 7.1 V, the light emission intensity of L1 changes according to the voltage applied thereto. When the difference between VA and VB becomes equal to or greater than 7.1 V, the voltage applied to L1 no longer changes and the light emission intensity becomes independent of the potential difference. When VA and VB are opposite in polarity, L2 emits light.

Diodes can also be used as alternatives for the Zener diodes. In general, the threshold voltage values of the diodes are about 1 V, and they do not change too significantly. For this reason, a plurality of diodes need to be connected in series to obtain threshold values falling within the desired range.

Figure 20:
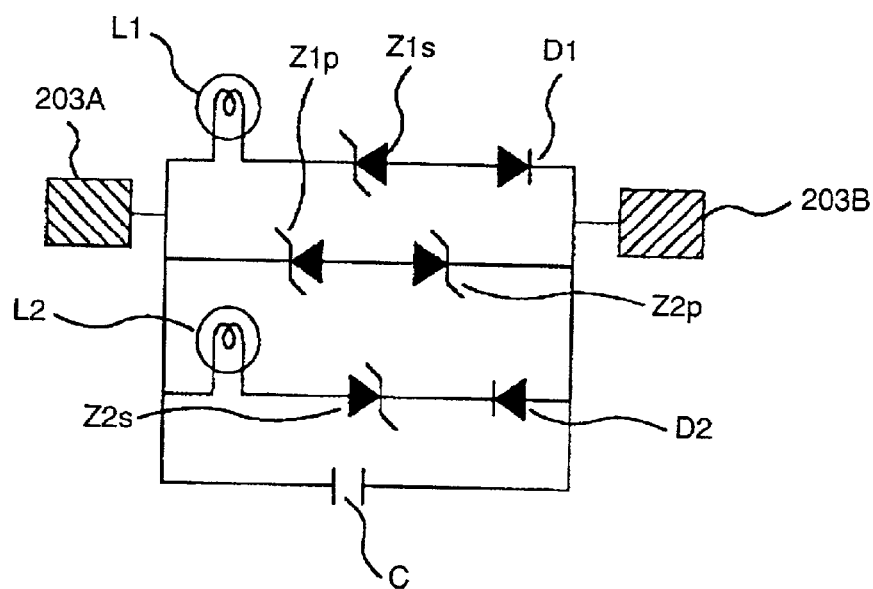
FIG. 20 is a schematic diagram of a potential difference measuring unit based on the present invention.

A modified version of the embodiment of FIG. 19 is shown in FIG. 20. In this version, four circuits are connected in parallel between antennas 203A and 203B. The first circuit consists of light-emitting element L1, Zener diode Z1, and diode D1, which are all connected in series. The Zener diode Z1 and the diode D1 are opposite in polarity. The second circuit, which includes light-emitting element L2, has the same composition as that of the first circuit, and all of its polarized components are reversed with respect to the polarized components of the first circuit. The third circuit consists of Zener diodes Z1p and Z2p connected in series, which are reversed in polarity with respect to one another. The fourth circuit consists only of capacitor C.

The light-emission condition of element L1 in such circuit composition can be expressed as VA−VB>VZ1s+VD1. The voltage applied to element L1 at this time can be expressed as (VZ1p+VZD2p)+(VZ1s+VD1), and the present invention, as with the embodiment of FIG. 19, provides a light-emitting element circuit protection function.

In FIGS. 19 and 20, when Zener diode Z1p (Z2p) connected in parallel to light-emitting element L1 (L2) is omitted, since the voltage applied to light-emitting element L1 (L2) is not limited, the light emission intensity and the VA−VB difference directly vary in the light emission range. Therefore, the potential difference between antennas A and B in the entire light emission range can be detected by measuring the light emission intensity. In this case, however, the possible flow of an overcurrent into light-emitting element L1 (L2) may damage the element L1 (L2).

In FIGS. 19 and 20, when diode D2 is omitted, the light-emitting element L2 emits light if VA−VB>VZD2. That is to say, both L1 and L2 emit light if VA−VB>VZD2 and VA−VB>VZ1+VD1. At this time, the VA−VB range can be further limited according to the light-emission conditions of L1 and L2.

In FIGS. 19 and 20, when Z1s (Z2s) is omitted, the light-emitting elements L1 and L2 emit light if VA−VB>VD1 and VB−VA>VD2, respectively.

Figure 21:
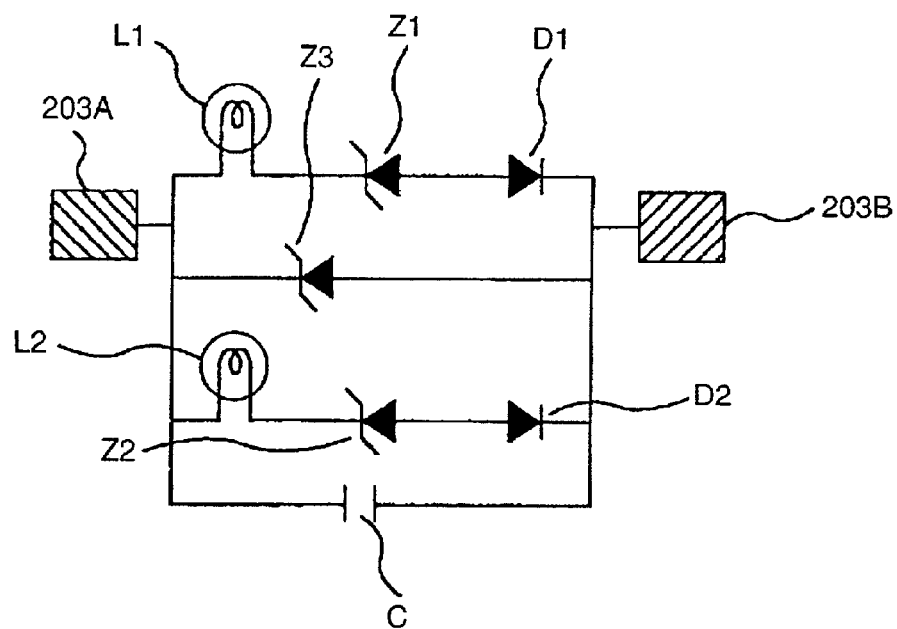
FIG. 21 is a schematic diagram of a potential difference measuring unit based on the present invention.

Next, the protection circuit 3 will be described with reference to FIG. 21. When the fact of VA>VB is known, light-emitting circuit composition can be simplified. For example, a case in which Zener diode Z2p is omitted from the embodiment of FIG. 20 is shown in FIG. 21. At this time, when elements are selected so that 0<VZ1+VD1<VZ2+VD2<VZ3 holds, only the light-emitting element L1 emits light under the condition of VA−VB>VZ1+VD1, and both L1 and L2 emit light under the condition of VZ1+VD1<VA−VB<VZ2+VD2. Also, since the maximum voltage applied to the light-emitting element L1 (L2) is VZ3+VZ1+VD1 (VZ3+VZ2+VD2), L1 (L2) is protected. It is possible to measure VA−VB by observing the intensity of the light emitted from L1 and L2.

The appropriate light-emitting circuit can be formed by adjusting the number of elements or combining them in the light-emitting circuits of FIGS. 19, 20, and 21, as required. In FIGS. 19, 20, and 21, although the light-emission voltage is described with reference to miniature lamps (or the like as the light-emitting elements), LEDs and other elements that have diode characteristics that slightly change in threshold voltage may be used. The principles of operation, however, are as described above. Also, when diodes are used as the light-emitting elements, diode D1 or D2 in series with respect to the elements in the embodiment of FIGS. 19, 20, and 21 is to be polarized in the same direction.

Figure 22:
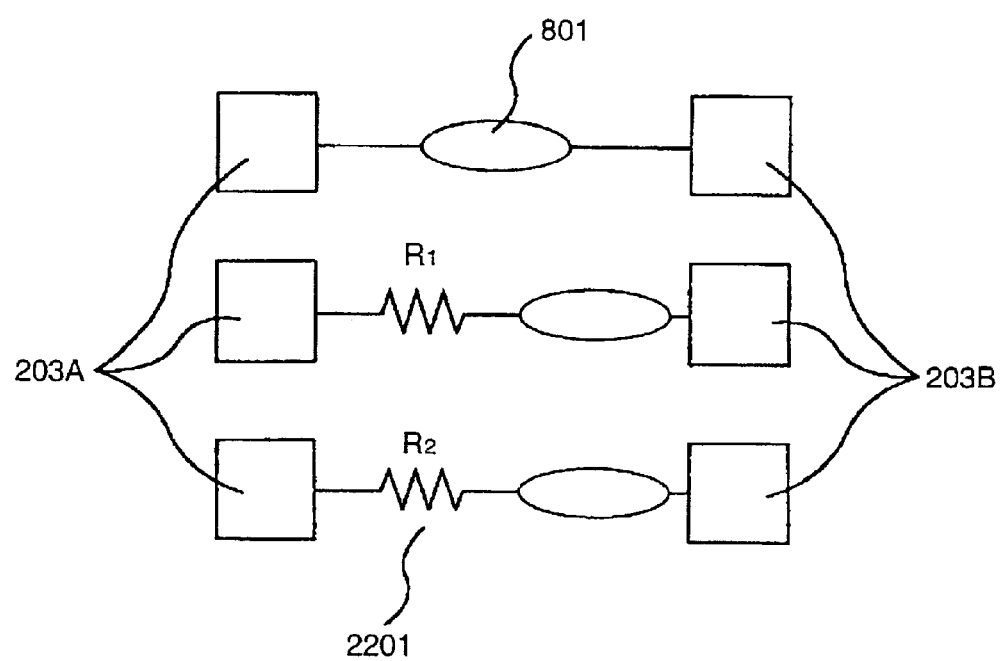
FIG. 22 is a schematic diagram of a potential difference measuring unit based on the present invention.

FIG. 22 shows a unit having a directly connected resistor 2201 to adjust the voltage applied to LED 801. This circuit composition can be used when the potential difference on the wafer is too great. Current I can be derived from the light emission intensity of LED 801. Voltage V1 across the LED can be derived from the current-voltage characteristics of the LED, and the voltage V2 across the resistor can be derived from I×R. The developed potential can be derived from V1+V2. In this circuit composition, a wide range of voltages can be measured at the same time by connecting resistors 2201 (R1 and R2) having different values to the respective LEDs 801.

FIG. 22 is a circuit diagram showing the fifth embodiment of the potential difference and current measuring portion used for potential difference measurement based on the present invention. This figure shows another example of a circuit composition intended to extend the range of the DC potential differences which can be measured using the potential difference and current measuring portion, and the resistance elements for limiting the flow of current into LEDs 801 are connected in series.

As shown in FIG. 22, the potential difference and current measuring unit 200 has resistance elements connected in series to a parallel-connected circuit consisting of LEDs 801. Since resistance elements 2201 are connected, this prevents an overcurrent from flowing into LEDs 801, and the DC potential difference between conductor antennas 203A and 203B is voltage-divided into the terminal-to-terminal voltage of LEDs 801 and the terminal-to-terminal voltage of resistance elements 2201. Thus, the voltage applied to LEDs 801 can be reduced below the DC potential difference between conductor antennas 203A and 203B, and the range of the DC potential differences which can be measured using the potential difference and current measuring unit can be correspondingly extended.

And, in this case as well, since the light emitted from LEDs 801 can be detected visually or through a CCD camera or the like, separate connection lead wires or probes are not required for the acquisition of the detection output signals.

Figure 23:
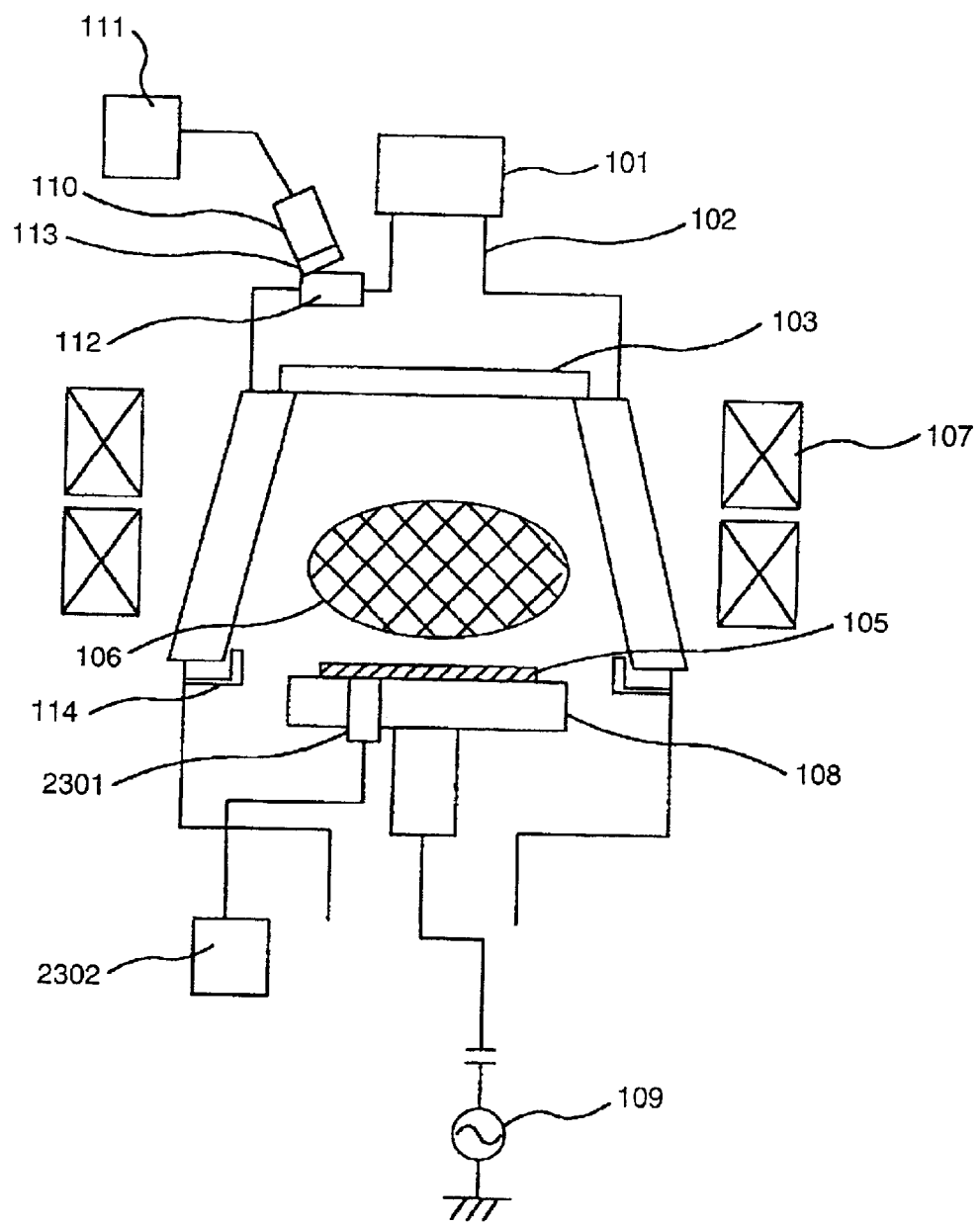
FIG. 23 is a diagram of an etching apparatus showing a method of observing light emission status in a potential difference measuring unit based on the present invention.
Figure 24:
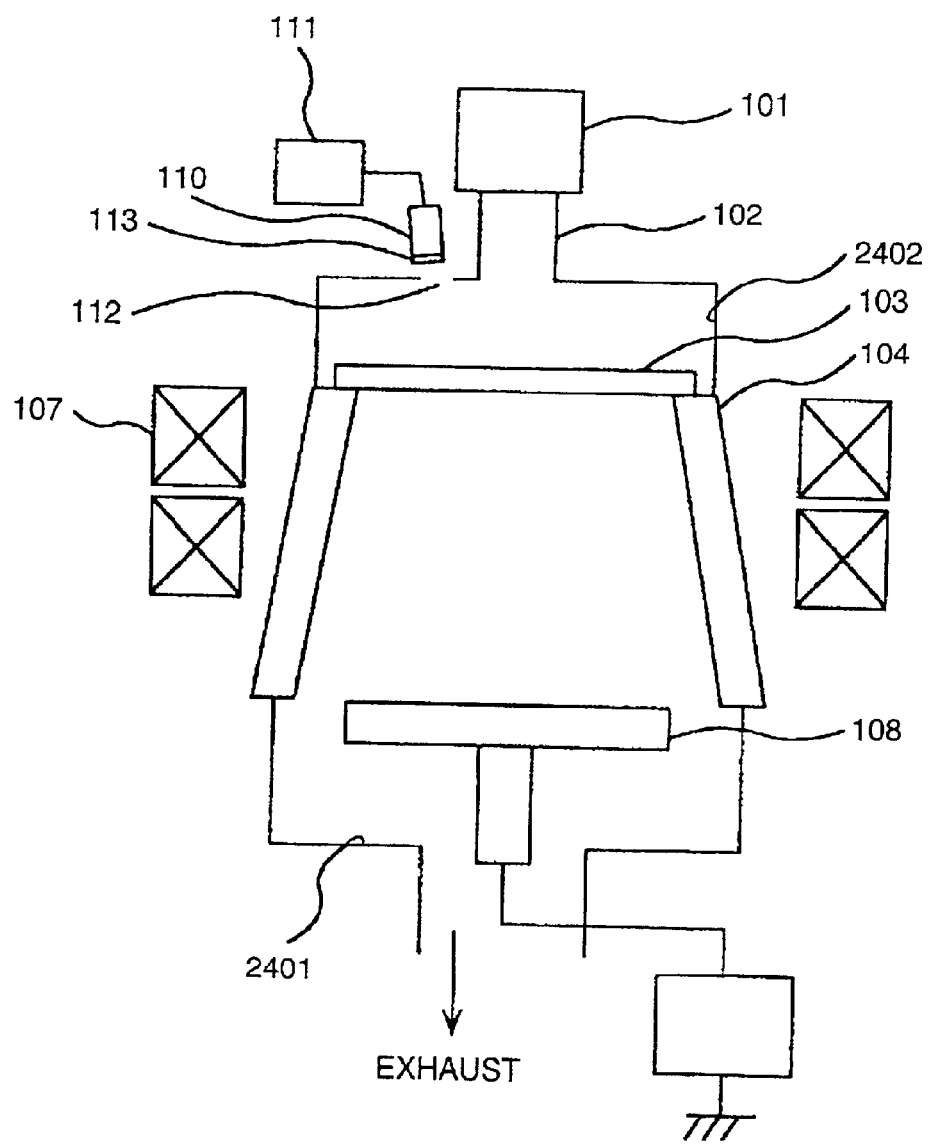
FIG. 24 is a diagram of an etching apparatus showing the installation location for a potential difference measuring unit based on the present invention.

Next, an observing method different from the above-described method of observing the light-emitting element through window 103 will be described. In the etching apparatus shown in FIG. 23, a measurement hole 2301 for a radiation temperature gauge is usually provided on sample mount 108 in order to measure the temperature of the silicon substrate 204. If no such hole is provided, sample mount 108 needs to be provided with a hole 2301 for observing the substrate 204. The intensity of light on substrate 204 can be observed using hole 2301, which extends to the surface of sample mount 108. At this time, when the appropriate light-emitting circuit 801 is selected so that the light emitted from light-emitting circuit 801 passes through the substrate 204, this substrate can be observed from the reverse side without ever having to provide the substrate with a hole. Similarly to the case in which the light emission status of light-emitting circuit 801 is observed from the surface of substrate 204, a camera 2302, an interference filter, a personal computer, and/or optical fibers are to be used as required.

Silicon, for example, has the property that it transmits light whose wavelength is about 1.3 microns or more. When substrate 204 is composed principally of silicon, therefore, the use of the L1450-35C LED having a wavelength of 1,450 nm makes it possible for the emitted light on the surface of substrate 204 to be observed from the reverse side of this substrate without ever having to provide it with a hole. This circuit composition, in such case, makes it unnecessary to provide the observation window 112.

The potential difference and current measuring unit of the present invention can be installed in various places. More specifically, the packaging of the potential difference and current measuring unit when mounted on an insulating object enables this package to be installed at any position and in any number of places. This package can also be installed on the inner wall of semiconductor manufacturing equipment to observe the status of this inner wall. The package usually also can be installed in an area not directly exposed to the effects of the plasma. This area includes, for example, the side of the sample mount 108, the wall surface of the reaction chamber facing the sample mount, or a position (say, 2401) directly above the vacuum-exhaust pump for the reaction chamber. The reason for this is to interrupt wafer processing immediately on detection of an unusual state during plasma monitoring and then provide corrective measures in order to return the plasma to a normal state. These measures refer to, for example, exposing the reaction chamber to the atmosphere and cleaning the wall of the reaction chamber and the flow channel of the exhaust system using an organic solvent or the like. Also, the potential difference between any two points can be measured using a package installed on the inner wall (for example, at position 2402) of waveguide 102.

Basically, the antennas are formed using conductors. For minimum metal pollution, however, impurity-doped poly-crystal silicon or a light metal (such as aluminum) or a highly electroconductive carbon should be used as the antenna material.

LEDs are usually made of a compound semiconductor such as gallium nitride (GaN) or AlGaN, but if such LEDs are inserted in externally exposed form into silicon-based semiconductor manufacturing equipment, metal pollution will result. To avoid this problem, the necessary section should be shielded with a suitable material which enables emitted light to be observed. Examples of this material include silicon oxide, plastic resin, and so on.

Figure 25A:
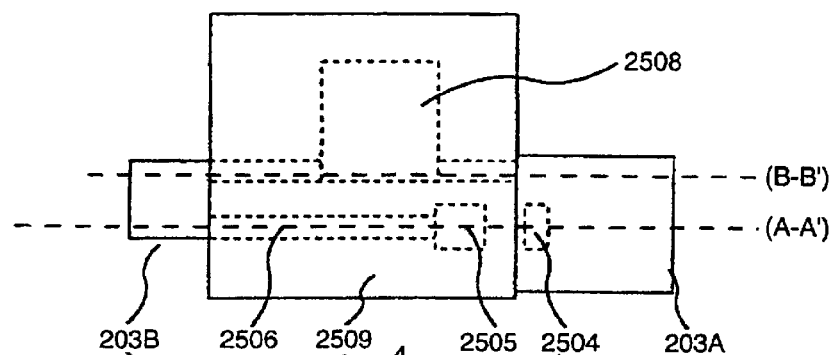
FIG. 25A is a top view of a potential difference measuring unit based on the present invention.
Figure 25B:
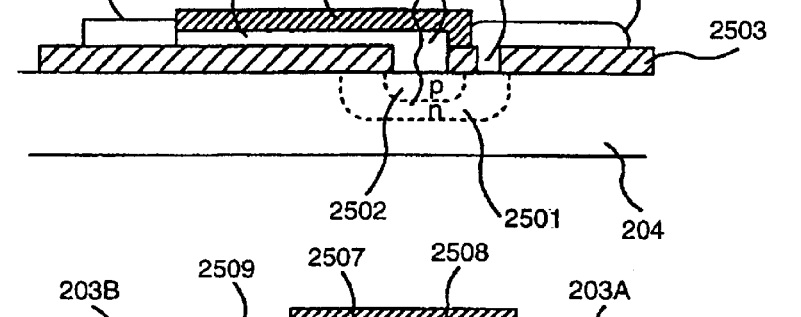
FIG. 25B is a cross-sectional view taken along line A–A' in FIG. 25A.
Figure 25C:
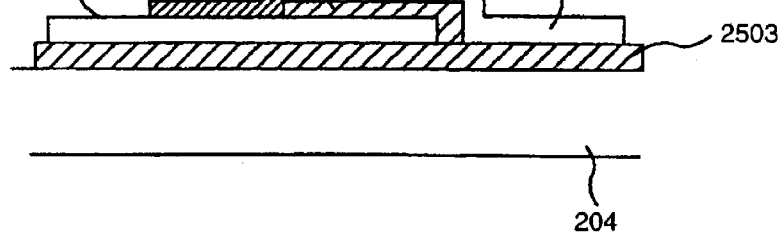
FIG. 25C is a cross-sectional view taken along line B–B' in FIG. 25A.

Next, an example of a GaAs light-emitting element is shown in FIGS. 25A, 25B, and 25C, which are diagrams showing the potential difference and current measuring unit 200 used for potential difference measurement based on the present invention, and showing an example of a potential difference and current measuring unit integrated with substrate 204 thereon. A top view of such a measuring unit is shown as FIG. 25A; a cross-sectional view taken along line A–A' of FIG. 25A is shown in FIG. 25B; and a cross-sectional view taken along line B–B' of FIG. 25A is shown in FIG. 25C.

The potential difference and current measuring unit 200 shown in FIGS. 25A to 25C has a potential difference and current measuring portion formed on the substrate 204 consisting of gallium arsenic (GaAs) and other substances. Light-emitting diodes consisting of n-type semiconductor area 2501 and p-type semiconductor area 2502 are formed on the substrate 204 by use of a method, such as ion implantation, and this p-n junction emits light. The first insulating film 2503 is formed on the substrate including the LED forming portion, and holes 2504 and 2505 that lead to substrate 204 are provided in the n-type semiconductor area 2501 and p-type semiconductor area 2502 of the first insulating film 2503. One end of the first conductor 2506 is connected to p-type semiconductor area 2502 through hole 2505, and the other end is routed along the first insulating film 2503.

One end of antenna 203A is connected to n-type semiconductor area 2501 through hole 2504, and the other end is routed along the first insulating film 2503. The conductor antenna 203B, after being connected to the other end of the first conductor 2506, is formed on the first insulating film 2503. The second insulating film 2507 is formed on part of the other conductor antenna 203B. The second conductor 2508, after being connected to conductor antenna 203A, is formed on the second insulating film 2507. The third insulating film 2509 is formed so as to ensure that the exposed portions of the first conductor 2506, the second conductor 2508, and conductor antenna 203B are covered with the insulating film, and that the first conductor 2506 and conductor antenna 203A are electrically insulated. In this case, the portion where conductor antenna 203B and the second conductor 2508 are arranged so as to face one another via the second insulating film 2507 constitutes a capacitor, which is connected in parallel to an LED.

According to this embodiment, since the LED emits light according to the particular DC potential difference between conductor antennas 203A and 203B on substrate 204, the DC potential difference can be measured by detecting the intensity of the emitted light.

In this case, the use of a light-transmitting substance (such as a poly-silicon) to form the second conductor 2508 and the third insulating film 2509 enables light to be radiated to the outside. Light can likewise be radiated to the outside by providing in its path a window that is covered with a transparent insulating film.

A light-emitting diode (LED) can likewise be formed by forming conductor antennas 203A and 203B on silicon substrate 204, or by forming a capacitor first, then embedding an LED microchip in the conductor antennas 203A/203B forming area or capacitor forming area by ion beam processing. Thus, a circuit of the same composition as that described above can be formed.

Although the embodiments described heretofore represent examples of measurement in a plasma etching apparatus, the present invention also enables similar measurement with a film deposition apparatus, a resist removal apparatus, and the like.

In addition, although the embodiments of semiconductor manufacturing equipment that have been described heretofore relate to a plasma source that mainly uses magnetic fields and microwaves, the invention can likewise be applied to other types of equipment that use a plasma source, such as equipment that uses high-frequency inductive coupling or capacitive coupling to generate a plasma, or equipment that uses electromagnetic waves of the UHF band to generate a plasma.

As described above, according to the present invention, it is possible to provide a potential difference and current measuring method that enables the DC potential difference on a target object to be measured using a simple means and a potential difference and current measuring portion of a simple configuration. In other words, it is possible to supply a means by which important quantities in a semiconductor surface treatment apparatus, that uses plasma, namely, the plasma potential difference and plasma current occurring on the surface of a wafer, are measured without the modification of the apparatus. Since the use of a camera enables non-contact measurement of emitted light intensity, the lead-in terminals for lead wires that are always required in conventional probing methods become unnecessary. In addition, since the target wafer does not require lead wire connection, wafers can be changed in the same way as performed for etching.

Furthermore, according to the present invention, it is possible to supply a highly efficient sample processing method that uses a potential difference and current measuring portion of a simple configuration.

What is claimed is:

1. A method of measuring the potential differences for plasma processing with a plasma processing apparatus that processes a sample by introducing a gas into vacuum chambers and generating plasma, wherein said method of measuring potential differences for plasma processing is characterized in that a light-emitting portion is formed on a measurement-use sample of the sample to be processed, a current flows into said light-emitting portion according to the potential difference that has been generated across said light-emitting portion, the intensity of the light emitted from said light-emitting portion according to the particular level of said current is measured, and the potential difference on said measurement-use sample according to the particular light intensity is measured.

2. A method of measuring the plasma currents for plasma processing during which the plasma processing of a sample is accomplished by introducing a gas into vacuum chambers and generating plasma, wherein said method of measuring plasma currents for plasma processing is characterized in that a light-emitting portion is formed on a measurement-use sample of the sample to be processed, the flow of charged particles from the plasma to the surface of said measurement-use sample is measured as the intensity of the light emitted from said light-emitting portion according to the level of the current flowing thereinto, and the amount of current flowing into said light-emitting portion according to the particular light intensity is measured.

3. An apparatus for measuring plasma potential differences and currents in a plasma processing apparatus that provides a sample with plasma processing by introducing a gas into vacuum chambers and generating plasma, wherein said potential difference and current measuring unit is characterized in that it has a light-emitting portion formed on a measurement-use sample of the sample to be processed, allowing a current to flow into said light-emitting portion according to the potential difference that has been generated across said light-emitting portion, and measuring the intensity of the light emitted from said light-emitting portion according to the particular level of said current, and measures the potential difference on said measurement-use sample according to the particular light intensity.

4. An apparatus for measuring plasma potential differences and currents in a plasma processing apparatus that provides a sample with plasma processing by introducing a gas into vacuum chambers and generating plasma, wherein said potential difference and current measuring unit is characterized in that it has a light-emitting portion formed on a measurement-use sample of the sample to be processed, and a means by which the flow of charged particles from the plasma to the surface of said measurement-use sample is measured as the intensity of the light emitted from said light-emitting portion according to the level of the current flowing thereinto, and measures the amount of current flowing into said light-emitting portion according to the particular light intensity.

5. A potential difference and current measuring method using a potential difference and current measuring portion provided with one pair of conductor antennas, a light-emitting portion connected between said pair of conductor antennas, and an alternating-current (AC) voltage bypass element connected to said light-emitting portion, wherein said potential difference and current measuring method is characterized in that when said pair of conductor antennas are arranged at and connected to the measuring positions on the object to be measured, light will be emitted from said light-emitting portion and the direct-current (DC) potential differences and DC currents at said measuring positions will be measured by the detection of the intensity of the emitted light.

6. A potential difference and current measuring method as set forth in claim 1, 2 or 5, wherein said potential difference and current measuring method is characterized in that said potential difference and current measuring portion consists of multiple potential difference and current measuring members arranged at and connected to the spaced measuring positions on the object to be measured.

7. A potential difference and current measuring method as set forth in claim 1, 2 or 5, wherein said potential difference and current measuring method is characterized in that said potential difference and current measuring portion consists of multiple potential difference and current measuring members arranged at and connected to the spaced measuring positions on the object to be measured, and in that the light-emitting portion of each potential difference and current measuring member consists of one or more light-emitting diodes or combination of one or more diodes and light-emitting elements using filaments.

8. A potential difference and current measuring method as set forth in claim 5, wherein said potential difference and current measuring method is characterized in that said light-emitting portion consists of the light-emitting diodes or combination of diodes and light-emitting elements using filament, one with positive polarity and the other with negative polarity, and in that the DC potential difference at said measuring position and the corresponding voltage polarity are judged by the detection of light emission or no light emission from the light-emitting diodes or light-emitting elements.

9. A potential difference and current measuring apparatus as set forth in claim 3 or 4, wherein said potential difference and current measuring apparatus is characterized in that said potential difference and current measuring portion consists of multiple potential difference and current measuring members arranged at and connected to the spaced measuring positions on the object to be measured.

10. A potential difference and current measuring unit as set forth in claim 3 or 4, wherein said potential difference and current measuring unit is characterized in that said potential difference and current measuring portion consists of multiple potential difference and current measuring members arranged at and connected to the spaced measuring positions on the object to be measured, and in that the light-emitting portion of each potential difference and current measuring member either consists of the light-emitting diodes or combination of diodes and light-emitting elements using filament.

11. A potential difference and current measuring unit as set forth in claim 9, wherein said potential difference and current measuring unit is characterized in that said light-emitting diodes are different in light-emission threshold voltage and light-emitting diodes are different in emission color as well.

12. A potential difference and current measuring unit as set forth in claim 9, wherein said potential difference and current measuring unit is characterized in that when the potential between two equivalent measuring position is measured, said light-emitting portion, which consists of the light-emitting diodes or combination of diodes and light-emitting elements using filaments, has its forward and reverse polarized diodes taken as one set.

13. A potential difference and current measuring unit as set forth in claim 9, wherein said potential difference and current measuring unit is characterized in that said light-emitting portion includes a thin gate oxide film in a semiconductor device.

14. A potential difference and current measuring unit as set forth in claim 9, wherein said potential difference and current measuring unit includes an AC voltage bypass element which comprises a capacitor.

15. A potential difference and current measuring method as set forth in claim 7, wherein said potential difference and current measuring method is characterized in that said potential difference and current measuring portion has resistor elements connected to said light-emitting portion either in series or in parallel.

16. A potential difference and current measuring method as set forth in claim 7, wherein said potential difference and current measuring method is characterized in that said potential difference and current measuring portion has optical fibers arranged adjacently to said light-emitting portion and in that light emission from said light-emitting portion is detected through said optical fibers.

17. A potential difference and current measuring method as set forth in claim 7, wherein said potential difference and current measuring method is characterized in that said measurement-use sample is a semiconductor wafer and in that said measuring positions are two spaced positions on said semiconductor wafer.

18. A potential difference and current measuring method as set forth in claim 7, wherein said potential difference and current measuring method is characterized in that the semiconductor wafer, which is said measurement-use sample, is located inside the plasma reactor that provides surface treatment.

19. A potential difference and current measuring method as set forth in claim 7, wherein said potential difference and current measuring method is characterized in that said light-emitting portion emits light of the wavelength that enables transmission through the semiconductor substrate used as said measurement-use sample.

20. A potential difference and current measuring method as set forth in claim 7, wherein said potential difference and current measuring method is characterized in that when the light emitted from said light-emitting portion is monitored, measurements are performed from the reverse side of the semiconductor substrate used as said measurement-use sample mentioned.

21. A potential difference and current measuring unit as set forth in claim 9, wherein said potential difference and current measuring unit is characterized in that it includes a light-emitting circuit having diodes connected in parallel to said light-emitting portion.

22. A potential difference and current measuring unit as set forth in claim 5, wherein said potential difference and current measuring unit is characterized in that in addition to the fact that the measuring unit uses a potential difference and current measuring portion provided with one pair of conductor antennas and a light-emitting portion connected between said pair of conductor antennas, a structure made of an easily removal insulating body is mounted on one antenna.

23. A potential difference and current measuring unit as set forth in claim 5, wherein said potential difference and current measuring unit is characterized in that said antennas are made of a light metal such as impurity-doped silicon, aluminum, or magnesium, or of electroconductive carbon.

24. An etching rate measuring apparatus characterized in that the conductor portions of antennas A and B are exposed in approximately plane form and in the form surrounded by an insulating body, respectively, and in that when the intensity of the light from the light-emitting portion connected between the antennas is measured, the time dependence of the light emission intensity is examined and the etching rate is measured from two factors: the time from the start of the emission to the end, and the thickness of the conductor portion of antenna B.

25. An etching rate measuring method characterized in that the conductor portions of antennas A and B are exposed in approximately plane form and in the form surrounded by an insulating body, respectively, and in that when the intensity of the light from the light-emitting portion connected between the antennas is measured, the time dependence of the light emission intensity is examined and the etching rate is measured from two factors: the time from the start of the emission to the end, and the thickness of the conductor portion of antenna B.

26. A method of optimizing a plasma etching apparatus designed so as to generate plasma by introducing a gas into vacuum chambers, wherein said plasma etching apparatus optimization method is characterized in that a potential difference and current measuring portion is installed inside said etching apparatus and in that operating parameters on the etching apparatus are optimized from the relationship between the gas introducing position, the shapes of the reaction chamber, sample mount, and other apparatus components, and the intensity of the light emitted from a light-emitting portion of the potential difference and current measuring portion.

27. A method of optimizing the plasma etching parameters used to generate plasma by introducing a gas into vacuum chambers, wherein said plasma etching parameter optimization method is characterized in that a potential difference and current measuring portion is installed inside said etching apparatus and in that etching parameters are optimized from the relationship between parameters, such as the type of gas to be introduced, the flow rate of the gas, and the magnitude of the power to be applied, and the intensity of the light emitted from a light-emitting portion of the potential difference and current measuring portion.

28. A sample processing method intended to process a sample by introducing a gas into vacuum chambers and generating plasma, wherein said sample processing method is characterized in that a means of measuring potential differences is so constructed as to ensure that a light-emitting portion is formed on a measurement-use sample of the sample to be processed and measure the intensity of the light emitted therefrom according to the particular amount of current, and that the potential difference on said measurement-use sample is measured according to the measured light intensity, in that each time said sample within said vacuum chamber is processed the required number of times, said potential difference is measured using said measurement-use sample, and in that if said potential difference exceeds the required value, the processing of said samples will be interrupted.

29. A sample processing method intended to process a sample by introducing a gas into vacuum chambers and generating plasma, wherein said sample processing method is characterized in that a means of measuring plasma currents is so constructed as to ensure that a light-emitting portion is formed on a measurement-use sample, that the flow of charged particles from the plasma to the surface of said measurement-use sample is measured as the intensity of the light emitted from said light-emitting portion according to the level of the current flowing thereinto, and that the amount of current flowing into said light-emitting portion according to the particular light intensity is measured, in that each time said sample within said vacuum chamber is processed the required number of times, the plasma current is measured using said measurement-use sample, and in that if said plasma current exceeds the required value, the processing of said samples will be interrupted.

30. A potential difference and current measuring unit as set forth in claim 10, wherein said potential difference and current measuring unit is characterized in that said light-emitting diodes are different in light-emission threshold voltage and light-emitting diodes are different in emission color as well.

31. A potential difference and current measuring unit as set forth in claim 10, wherein said potential difference and current measuring unit is characterized in that when the potential between two equivalent measuring position is measured, said light-emitting portion, which consists of the light-emitting diodes or combination of diodes and light-emitting elements using filaments, has its forward and reverse polarized diodes taken as one set.

32. A potential difference and current measuring unit as set forth in claim 10, wherein said potential difference and current measuring unit is characterized in that said light-emitting portion includes a thin gate oxide film in a semiconductor device.

33. A potential difference and current measuring unit as set forth in claim 10, wherein said potential difference and current measuring unit includes an AC voltage bypass element comprises a capacitor.

* * * * *